(12) United States Patent
Sundvor et al.

(10) Patent No.: US 12,203,930 B2
(45) Date of Patent: Jan. 21, 2025

(54) SYSTEM AND METHOD FOR DETECTING TARGET SUBSTANCES

(71) Applicant: Nima Acquisition, LLC, Northfield, IL (US)

(72) Inventors: Scott Sundvor, San Francisco, CA (US); Ian Wallhead, San Francisco, CA (US); Joseph Horrell, San Francisco, CA (US); John Artiuch, San Francisco, CA (US); Dane Weitmann, San Francisco, CA (US); Stephen Wilson, San Francisco, CA (US); Steven Portela, San Francisco, CA (US); Jingqing Zhang, San Francisco, CA (US); Francisco Dias Lourenco, San Francisco, CA (US)

(73) Assignee: NIMA Partners, Inc., Waltham, MA (US)

( * ) Notice: Subject to any disclaimer, the term of this patent is extended or adjusted under 35 U.S.C. 154(b) by 0 days.

(21) Appl. No.: 17/819,479

(22) Filed: Aug. 12, 2022

(65) Prior Publication Data
US 2023/0071804 A1 Mar. 9, 2023

Related U.S. Application Data

(60) Continuation of application No. 16/403,124, filed on May 3, 2019, now Pat. No. 11,422,130, which is a
(Continued)

(51) Int. Cl.
*G01N 33/543* (2006.01)
*G01N 21/17* (2006.01)
(Continued)

(52) U.S. Cl.
CPC ....... *G01N 33/54366* (2013.01); *G01N 21/17* (2013.01); *G01N 33/02* (2013.01); *G01N 33/5308* (2013.01); *G01N 2021/1765* (2013.01)

(58) Field of Classification Search
CPC .. G01N 33/54366; G01N 21/17; G01N 33/02; G01N 33/5308; G01N 2021/1765
See application file for complete search history.

(56) References Cited

U.S. PATENT DOCUMENTS 3,802,842 A 4/1974 Lange et al.
4,066,511 A 1/1978 Montagnon
(Continued)

FOREIGN PATENT DOCUMENTS

CN 101909757 A 12/2010
EP 1640718 A1 3/2006
(Continued)

OTHER PUBLICATIONS

Neogen Corporation, Food Allergen Handbook, Ninth Edition, Copyright 2012, 28 pages.
(Continued)

*Primary Examiner* — Brian J. Sines
(74) *Attorney, Agent, or Firm* — McCarter & English, LLP

(57) ABSTRACT

A method includes capturing a signal of a detection substrate exposed to a sample containing a target substance; determining that the detection substrate is in a testable state; and generating an assessment of the presence of the target substance in the sample.

20 Claims, 17 Drawing Sheets

Related U.S. Application Data division of application No. 15/280,464, filed on Sep. 29, 2016, now Pat. No. 10,466,236, which is a continuation-in-part of application No. 14/498,298, filed on Sep. 26, 2014, now Pat. No. 9,939,432, which is a continuation-in-part of application No. 14/227,543, filed on Mar. 27, 2014, now Pat. No. 9,939,431.

(60) Provisional application No. 62/234,751, filed on Sep. 30, 2015, provisional application No. 61/874,590, filed on Sep. 6, 2013, provisional application No. 61/806,425, filed on Mar. 29, 2013.

(51) Int. Cl.
*G01N 33/02* (2006.01)
*G01N 33/53* (2006.01)

(56) References Cited

U.S. PATENT DOCUMENTS

| | | |
|---|---|---|
| 4,250,256 A | 2/1981 | Wielinger et al. |
| 4,822,174 A | 4/1989 | Deibel |
| 4,960,691 A | 10/1990 | Gordon et al. |
| 5,143,084 A | 9/1992 | Macemon et al. |
| 5,217,905 A | 6/1993 | Marchand et al. |
| 5,256,372 A | 10/1993 | Brooks et al. |
| 5,415,994 A | 5/1995 | Imrich et al. |
| 5,504,013 A | 4/1996 | Senior |
| 6,136,549 A | 10/2000 | Feistel |
| 6,136,610 A | 10/2000 | Polito et al. |
| 6,180,335 B1 | 1/2001 | Wilkins et al. |
| 6,319,466 B1 | 11/2001 | Markovsky et al. |
| 6,528,323 B1 | 3/2003 | Thayer et al. |
| 6,616,893 B1 | 9/2003 | Pham |
| 6,663,833 B1 | 12/2003 | Stave et al. |
| 6,881,554 B2 | 4/2005 | DiCesare et al. |
| 7,098,040 B2 | 8/2006 | Kaylor et al. |
| 7,220,597 B2 | 5/2007 | Zin et al. |
| 7,238,322 B2 | 7/2007 | Wang et al. |
| 7,267,799 B1 | 9/2007 | Borich et al. |
| 7,300,197 B2 | 11/2007 | McCurdy et al. |
| 7,371,582 B2 | 5/2008 | Nahm et al. |
| 7,507,374 B2 | 3/2009 | Gould et al. |
| 7,527,765 B2 | 5/2009 | Royds |
| 7,560,272 B2 | 7/2009 | Ramsey et al. |
| 7,585,529 B2 | 9/2009 | Villar et al. |
| 7,749,771 B2 | 7/2010 | Burgess-Cassler et al. |
| 7,776,266 B2 | 8/2010 | Royds |
| 7,784,678 B2 | 8/2010 | Kuo et al. |
| 7,932,099 B2 | 4/2011 | Egan et al. |
| 7,972,871 B2 | 7/2011 | Chandler |
| 7,995,196 B1 | 8/2011 | Fraser |
| 8,211,715 B1 | 7/2012 | Royds |
| 8,231,548 B2 | 7/2012 | Hoenes |
| 8,278,091 B2 | 10/2012 | Rutter et al. |
| 8,361,460 B2 | 1/2013 | Morimatsu et al. |
| 8,632,730 B2 | 1/2014 | Petrilla et al. |
| 9,005,551 B2 | 4/2015 | Chen et al. |
| 9,201,068 B2 | 12/2015 | Suni et al. |
| 9,285,331 B2 | 3/2016 | Minteer et al. |
| 9,625,357 B2 | 4/2017 | Bransky et al. |
| 10,533,995 B2 | 1/2020 | Sundvor et al. |
| 2003/0138819 A1 | 7/2003 | Gong et al. |
| 2003/0138941 A1 | 7/2003 | Gong et al. |
| 2003/0186458 A1 | 10/2003 | DiCesare et al. |
| 2004/0018575 A1 | 1/2004 | Rappin et al. |
| 2004/0022687 A1 | 2/2004 | Wuske et al. |
| 2004/0132091 A1 | 7/2004 | Ramsey |
| 2004/0137137 A1 | 7/2004 | Villar et al. |
| 2004/0141879 A1 | 7/2004 | Loomis et al. |
| 2004/0152209 A1 | 8/2004 | Zin |
| 2004/0189311 A1 | 9/2004 | Glezer et al. |
| 2004/0265234 A1 | 12/2004 | Morimatsu |
| 2005/0112779 A1 | 5/2005 | Wei et al. |
| 2005/0136553 A1 | 6/2005 | Kaylor |
| 2005/0147532 A1 | 7/2005 | Bellet et al. |
| 2005/0214866 A1 | 9/2005 | McCall et al. |
| 2005/0214951 A1 | 9/2005 | Nahm |
| 2005/0255533 A1 | 11/2005 | Dantini et al. |
| 2006/0051237 A1 | 3/2006 | Wang |
| 2006/0204399 A1 | 9/2006 | Freeman et al. |
| 2006/0240568 A1* | 10/2006 | Petruno .................. G01N 21/17 436/514 |
| 2006/0292035 A1 | 12/2006 | Gould |
| 2007/0041624 A1 | 2/2007 | Cork et al. |
| 2007/0047382 A1 | 3/2007 | McCurdy |
| 2007/0054414 A1 | 3/2007 | Burgess-Cassler et al. |
| 2007/0116595 A1 | 5/2007 | Petrilla |
| 2007/0238102 A1 | 10/2007 | Song |
| 2007/0238138 A1 | 10/2007 | Royds |
| 2007/0292899 A1 | 12/2007 | Lovell et al. |
| 2007/0292941 A1 | 12/2007 | Handique et al. |
| 2008/0171397 A1 | 7/2008 | Hardcastle et al. |
| 2008/0181821 A1 | 7/2008 | Jung et al. |
| 2008/0199851 A1 | 8/2008 | Egan |
| 2009/0047691 A1 | 2/2009 | Huwig et al. |
| 2009/0136633 A1 | 5/2009 | Royds |
| 2009/0148933 A1 | 6/2009 | Battrell et al. |
| 2009/0154776 A1 | 6/2009 | Mott et al. |
| 2010/0129922 A1 | 5/2010 | Gold et al. |
| 2010/0167309 A1 | 7/2010 | Chandler |
| 2010/0210033 A1 | 8/2010 | Scott |
| 2010/0222224 A1 | 9/2010 | Suni |
| 2010/0255609 A1 | 10/2010 | Rutter |
| 2010/0317033 A1 | 12/2010 | Abdel |
| 2011/0039198 A1 | 2/2011 | Ashley et al. |
| 2011/0044865 A1 | 2/2011 | Groisman et al. |
| 2011/0059550 A1 | 3/2011 | Haik |
| 2011/0143968 A1 | 6/2011 | Chen |
| 2012/0046203 A1 | 2/2012 | Walsh et al. |
| 2012/0078455 A1 | 3/2012 | Chrostowski et al. |
| 2012/0264232 A1 | 10/2012 | Kramer et al. |
| 2013/0203043 A1 | 8/2013 | Ozcan et al. |
| 2014/0033809 A1 | 2/2014 | Bransky |
| 2014/0072960 A1* | 3/2014 | Lansing .............. G01N 33/571 435/7.1 |
| 2014/0116158 A1* | 5/2014 | Minteer .................. G01N 33/02 73/863.01 |
| 2014/0120563 A1 | 5/2014 | Ozcan et al. |
| 2014/0125835 A1 | 5/2014 | Voss et al. |
| 2014/0174953 A1 | 6/2014 | Elder et al. |
| 2014/0186880 A1 | 7/2014 | Lowenkamp, Jr. |
| 2014/0227796 A1 | 8/2014 | Gold et al. |
| 2014/0295406 A1 | 10/2014 | Sundvor et al. |
| 2014/0300696 A1 | 10/2014 | Ozcan et al. |
| 2015/0011020 A1 | 1/2015 | Sundvor et al. |
| 2015/0072358 A1 | 3/2015 | Luckert |
| 2015/0151300 A1 | 6/2015 | Williams et al. |
| 2017/0003222 A1 | 1/2017 | Neijzen et al. |
| 2019/0086430 A1 | 3/2019 | Wang |

FOREIGN PATENT DOCUMENTS

| | | |
|---|---|---|
| WO | 9914595 A1 | 3/1999 |
| WO | 2005031351 A1 | 4/2005 |
| WO | 2006117129 A1 | 11/2006 |
| WO | 2011039198 A2 | 4/2011 |
| WO | 2012078455 A1 | 6/2012 |
| WO | 2014047692 A1 | 4/2014 |
| WO | 2014176556 A1 | 10/2014 |
| WO | 2015017442 A2 | 2/2015 |

OTHER PUBLICATIONS

Wen et al., A Novel Extraction Method for Peanut Allergenic Proteins in Chocolate and Their Detection by a Liposome-Based Lateral Flow Assay, European Food Research and Technology, 2005, 221(3-4):564-569.

Woodfolk et al., Allergens, Sources, Particles, and Molecules: Why Do We Make IgE Responses?, Allergology International, 2015, 64(4):295-303.

(56) References Cited

OTHER PUBLICATIONS

PCT International Search Report and Written Opinion, PCT/US2014/032006, Aug. 13, 2014, 10 pages.
PCT International Search Report and Written Opinion, PCT/US2014/057776, Jan. 14, 2015, 11 pages.
PCT International Search Report and Written Opinion, PCT/US2016/054494, Feb. 16, 2017, 12 pages.
The State Intellectual Property Office of People's Republic of China, First Office Action and Search Report, Application No. 201480018850.2, May 11, 2016, 11 pages.
The State Intellectual Property Office of People's Republic of China, Second Office Action, Application No. 201480018850.2, Feb. 7, 2017, 12 pages.
The State Intellectual Property Office of People's Republic of China, Third Office Action, Application No. 201480018850.2, Oct. 10, 2017, 8 pages.
The State Intellectual Property Office of People's Republic of China, Office Action and Search Report, Application No. 201480079288.4, Jan. 30, 2019, 10 pages.
European Patent Office, Extended Search Report, Application No. 14774530.1, Sep. 26, 2016, 8 pages.
European Patent Office, Extended Search Report, Application No. 14887682.4, Oct. 13, 2017, 8 pages.

* cited by examiner

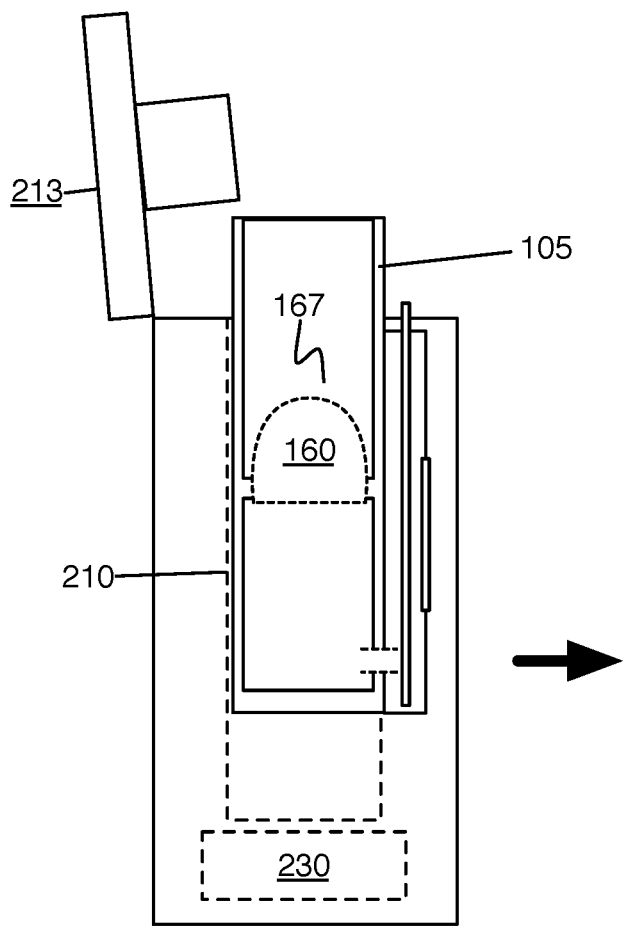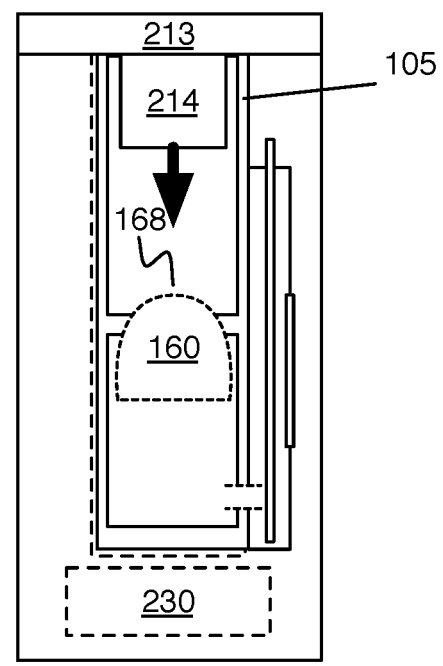
FIGURE 8D
FIGURE 8E

Pre-processing Image of 150

Post-processing Image of 150

SYSTEM AND METHOD FOR DETECTING TARGET SUBSTANCES

CROSS-REFERENCE TO RELATED APPLICATIONS

This application is a Continuation of U.S. Application Ser. No. 16/403,124 filed on 3 May 2019, which is a Divisional Application of U.S. application Ser. No. 15/280,464 filed on 29 Sep. 2016 which is a Continuation-In-Part Application of U.S. application Ser. No. 14/498,298, filed on 26 Sep. 2014, which is a Continuation-In-Part Application of U.S. application Ser. No. 14/227,543, filed on 27 Mar. 2014, which claims the benefit of U.S. Provisional Application No. 61/874,590, filed on 6 Sep. 2013, and U.S. Provisional Application No. 61/806,425, filed on 29 Mar. 2013, which are each incorporated herein in their entirety by this reference. U.S. application Ser. No. 15/280,464 filed on 29 Sep. 2016 claims priority to U.S. Provisional Application No. 62/234,751 filed on 30 Sep. 2015, which is incorporated in its entirety by this reference.

TECHNICAL FIELD

This invention relates generally to the consumer assay device field, and more specifically to an improved system and method for detection of target substances within a consumable.

BACKGROUND

A wide variety of consumables (e.g., foods, beverage, cosmetics, etc.) contain contaminants, toxins, allergens, and/or other substances that are of interest to all or specific types of consumers. In particular, in recent years, an increase in the number of consumers with an identified allergy (e.g., gluten allergy, dairy allergy, fish allergy, nut allergy, soy allergy, cosmetic allergy, etc.) has contributed to a number of products that omit ingredients having an associated allergen; however, such consumers are still at risk for consuming items with a harmful substance when the items do not have adequate labeling or documentation. Various systems and methods exist for detection of toxins and harmful substances present in a sample; however, current systems and methods are deficient due to one or more of: a time-intensive manner of receiving test results, a labor-intensive manner of receiving test results, a non-automated manner of processing samples, system bulk, system non-portability, and other factors that contribute to inconveniencing a consumer using such systems.

Due to these and other defects of current systems and methods for detecting harmful substances in consumables, there is thus a need for an improved system and method for detecting target substances. This invention provides such a system and method.

BRIEF DESCRIPTION OF THE FIGURES

FIGS. 8A-E depict variations and configurations of a portion of a system for detection of harmful substances;

DESCRIPTION OF THE PREFERRED EMBODIMENTS

The following description of preferred embodiments of the invention is not intended to limit the invention to these preferred embodiments, but rather to enable any person skilled in the art to make and use this invention.

1. Overview

Figure 1:
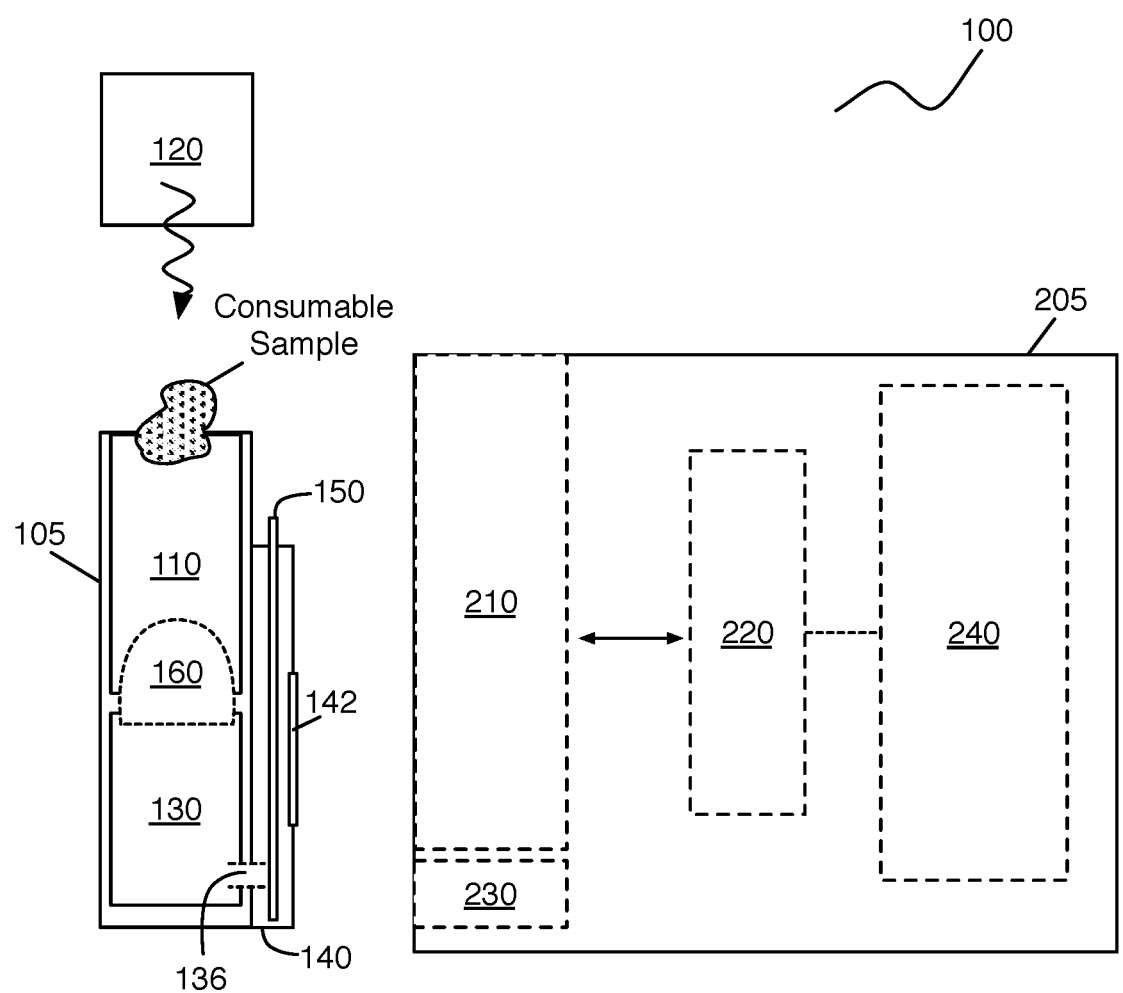
FIG. 1 depict an embodiment of a system for detection of harmful substances.

As shown in FIG. 1, an embodiment of a system 100 for detecting a target substance in a consumable sample includes: a test container 105 and an analysis device 205 configured to detect presence of the harmful substance at the test container 105. In an embodiment, the test container 105 includes: a sample processing chamber 110 for receiving and processing the consumable sample, and a detection substrate 150 fluidly connected to the sample processing chamber for detection of the harmful substance. In an embodiment, the analysis device 205 includes: a housing 210 configured to receive the test container 105, a mixing module 230 configured to mix the homogenized sample within the test container with a process reagent, an optical sensing subsystem 220 mounted to the housing and configured to enable detection of presence of the harmful substance at the detection substrate 150, and a processing and control system 240 configured to receive and process signals from the optical sensing subsystem 220, thereby producing an output indicative of presence of the harmful substance in the consumable sample.

The system 100 functions to receive and process a sample of a consumable (e.g., food, beverage, cosmetic, etc.), and detect the presence of a target substance in the sample. In examples, the target substances can be a harmful substance, and can include any one or more of: an allergen (e.g., gluten allergen, a dairy-derived allergen, a nut allergen, a fish allergen, an egg-derived allergen, etc.) a toxin, a bacterium, a fungus, a pesticide, a heavy metal, a chemical or biological compound (e.g., a fat, a protein, a sugar, a salt, etc.), and any other suitable harmful substance. In alternative examples, the target substance can be a benign substance, or any other desired target substance found in consumables. The system 100 is preferably configured to impose minimal requirements upon a consumer using the system 100, in terms of labor-intensiveness, time-intensiveness, and cost-intensiveness. As such, the system 100 is preferably configured to automatically or semi-automatically process the sample in a manner that is intuitive to the consumer, and to quickly provide information regarding presence of the harmful substance(s) within the sample. The system 100 is preferably configured to provide repeatable and reliable results to the consumer, to prevent false-positive and false-negative detection of target substances, and to avoid misinterpretation of the results by the consumer. As such, the system 100 is preferably configured to automatically interpret the signals received from the optical sensing subsystem, and to automatically provide the output indicative of the presence of the target substance to the consumer. The system 100 is preferably configured to be portable and compact, such that the user can conveniently carry the system 100 during his/her daily life (e.g., to establishments); however, in some alternative variations, the system 100 can be configured to be non-portable and/or non-compact. Preferably, the system 100 has reusable and disposable components, and in some variations portions of the system 100 are configured to be single-use (e.g., the test container(s), portions of a test container, the detection substrate) while other portions of the system 100 are configured to be reusable (e.g., the analysis device). However, in other variations, the system 100 can include only reusable components or only disposable components.

In an example workflow utilizing the system 100, the system 100 is configured to receive a sample at a sample processing chamber 110 of a test container 105, to homogenize the sample, to mix the homogenized sample with at least one process reagent, to flow the homogenized sample to a beginning portion of a detection substrate 150, to capture an image of the detection substrate 150 with an optical sensing subsystem 220, and to process the captured image to enable detection of one or more harmful substances within the sample at an analysis device. In the example workflow, a user of the system 100 would deposit the sample into the test container, perform a small amount of labor to facilitate homogenization of the sample, and place the container in the analysis device for further processing and analysis of the sample, such that the user has minimal interaction with the system 100 in generating an output.

Figure 14:
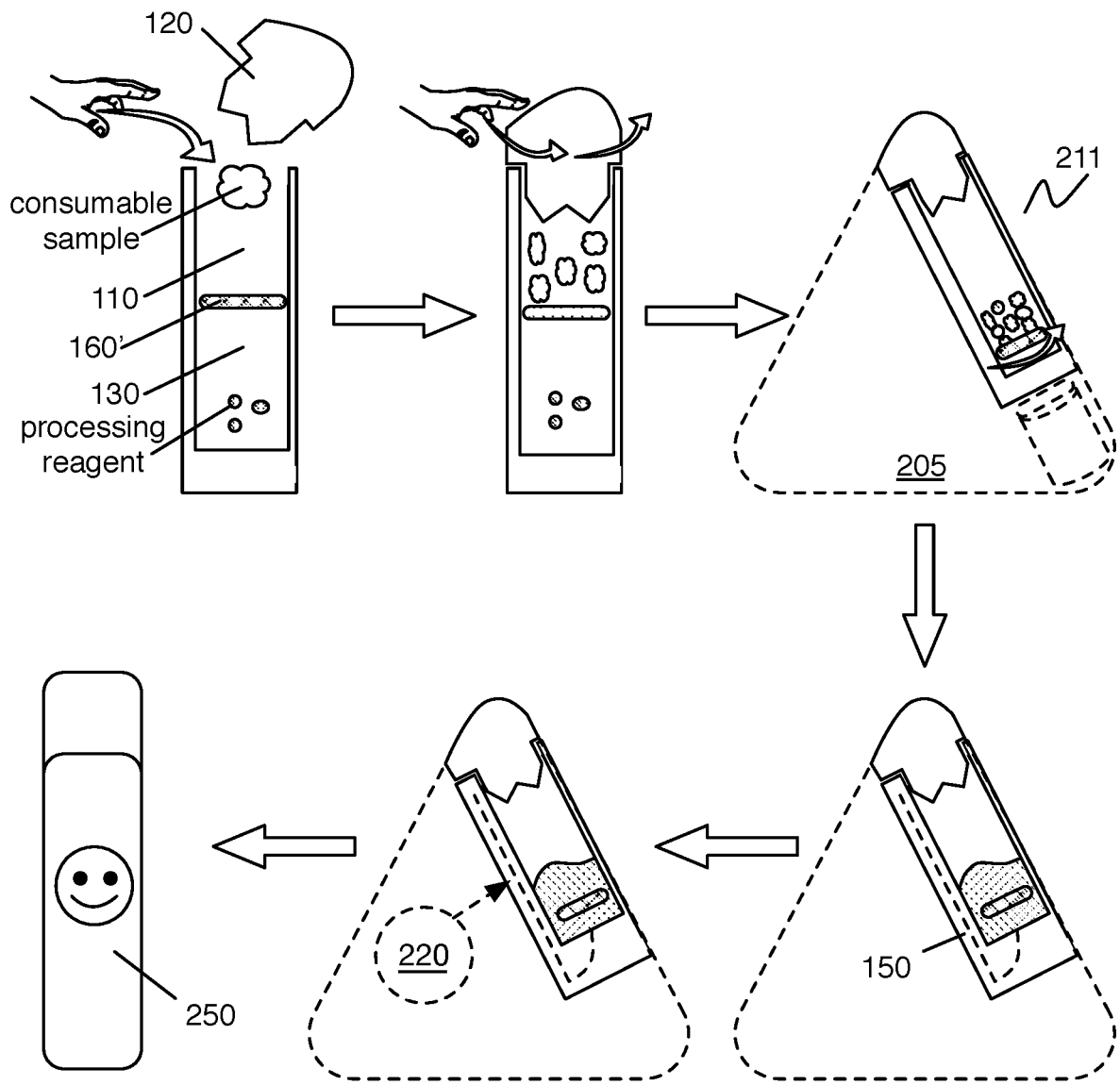
FIG. 14 depicts a schematic of an embodiment of a system for detection of harmful substances.

As shown in FIG. 14, in another example workflow, the system 100 can function to mix the homogenized sample (e.g., where the system 100 is configured to rotate a mixing element located within the sample processing chamber of the test container) with the appropriate processing reagents, to flow the consumable sample to a beginning portion of a detection substrate 150 (e.g., test strip), to perform optical analysis with an optical sensing subsystem 220 of a complementary analysis device 205, and to display results on a user interface 250 (e.g., an indicator of whether or not allergens were detected). In this example workflow, the optical analysis would be performed by the processing module of the analysis device, and can include capturing a plurality of images of the detection substrate at various time points, as well as performing various image processing routines on each captured image (e.g., convolution, averaging, thresholding, peak detection, calibration, etc.) in generating an output.

As such, the system is preferably configured to facilitate implementation of the method 300 described in Section 4 below; however, the system 100 can additionally or alternatively be configured to perform any other suitable method.

2. Benefits

In specific examples, the system 100 and/or method 300 can confer several benefits over conventional methodologies used for detecting target substances in a sample. For example, conventional methodologies for allergen testing (e.g., mass spectroscopy, PCR techniques, standard ELISA, etc.), can be expensive, not currently suitable for consumer use, involve many processing steps, are unable to detect target proteins (e.g., that can cause an allergic response), have results that are difficult to interpret (e.g., requiring specialized knowledge), are not robustly effective for various sources of target substances, and/or have limited accuracy. In specific examples, the system 100 and/or method 300 can perform one or more of the following:

First, the technology can provide an intuitive, consumer-friendly allergen testing device for detecting allergens in consumable samples while requiring minimal human interaction with the device. For example, the technology can perform detection of potentially life-threatening allergens while only asking the user to insert a consumable sample (e.g., a food sample, a drink sample, etc.) into a test container, seal the test container, and place the test container into an analysis device, which subsequently performs an automated analysis of the sample to determine the presence of the allergen of interest.

In a specific example, the action of placing the test container into the analysis device can cause the processing module of the analysis device to (1) control the mixing module to mix the homogenized sample with processing reagents to produce a mixed liquid sample, which then contacts the detection substrate and flows laterally along the detection substrate, (2) capture an image of the exposed detection substrate using the optical sensing subsystem of the analysis device, and (3) process the captured image in order to detect the presence of the allergen of interest. Automating the interpretation of the results of the lateral flow assay can improve the accuracy and repeatability of the analysis, thereby reducing risk to the consumer of encountering a harmful allergen. In another specific example, the test container can define a keyed profile with asymmetric sides and/or ends of the test container, thereby ensuring that the test container can only be inserted into the analysis device in a single direction and/or angular orientation and that the detection substrate is thus correctly oriented for image capture and processing by the analysis device. Further, the technology can possess a form factor and design enabling discreteness and/or portability. For example, the technology can be handheld, mobile and/or possess a footprint enabling the technology to be easily transported (e.g., in a purse, in a pocket, in a backpack, etc.) for on-the-go allergen testing (e.g., at a restaurant, at a workplace, etc.).

Second, the technology can quickly provide allergen testing results so as to provide a seamless eating experience. In a specific application, the technology can provide an indication and/or an analysis of presence of gluten in a food sample on the order of minutes (e.g., less than 3 minutes), using an improved allergen extraction process, streamlined and automatic sample processing, and an improved analysis protocol (e.g., using a detection substrate on which regions exposed to the allergen of interest absorb a specific frequency of light, and exposing the detection substrate to light of predominantly that frequency and measuring the quantity of light absorbed by the substrate). However, variations of the specific application can additionally or alternatively involve detection of any other suitable type or number of allergens (e.g., gluten allergen, a dairy-derived allergen, a nut allergen, a fish allergen, an egg-derived allergen, a soy derived allergen, a peanut-derived allergen, shellfish-derived allergens, etc.) and/or any other substances of interest in a consumable sample, within any other suitable timeframe, and/or using any other suitable substance indicator module.

Third, the technology provides an efficient, user-friendly device while detecting allergens with high specificity. In a specific application, the test container and analysis device can identify if a consumable sample has 20 parts per million (ppm) or more of gluten. Additionally or alternatively, the technology can identify any suitable combination or concentration of allergens, in order to detect allergens at a specificity matching FDA guidelines for restaurants to label consumables as free of a given allergen. Further, the technology can detect with such specificity while requiring a minimal amount of consumable sample, so as to not significantly remove portions of the consumable for other purposes (e.g., consumption).

Fourth, the technology can be designed to achieve the above-mentioned functionality while retaining an unobtrusive design. For example, the morphological form of a test container can be reduced by efficiently positioning and orienting components within the test container, while strategically directing sample flow through the components of the test container. In a specific example of efficient positioning of components, a capillary-flow based detection substrate can be positioned laterally adjacent to a grinding chamber situated above a mixing chamber. In a specific example strategic directing of sample flow, the flow can include gravitationally driven flow along both the longitudinal axis and lateral axis of the test container in order to leverage both downward gravitational flow and upward capillary flow. Further, the technology can be assembled with materials complementing the strategic design. For example, the analysis device(s) and/or test container(s) can incorporate double shot plastics to improve durability while retaining functionality.

The technology can, however, provide any other suitable benefit(s) in the context of detecting target substances in consumable and/or non-consumable samples.

3. System

As discussed above, the system can include: a test container 105 that includes: a sample processing chamber 110 for receiving the consumable sample, generating a homogenized sample upon processing of the consumable sample, combining the homogenized sample with a process reagent to produce a dispersion, and exposing the dispersion to a detection substrate 150 for detection of the harmful substance.

The consumable sample is preferably a food sample potentially containing a harmful substance (e.g., an allergen), and is preferably an unprocessed food sample, such that the user can gather an insubstantial volume of a food substance that he/she intends to consume for a meal, and deliver it into the sample processing chamber 110 of the test container 105 for processing and analysis. In this example, the food sample can include a mixture of different food items (e.g., different components of an entree), can include a single food item (e.g., a single component of an entree), and/or can include a sequence of different food items (e.g., a sequence of components from an entree). The food sample can be cored, spooned, tweezed, and/or processed from a bulk volume of food in any other suitable manner. However, in variations, the consumable sample can include any one or more of a: beverage sample (e.g., volume of a mixed drink), cosmetic substance (e.g., volume of makeup, volume of lotion, volume of fragrance, volume of soap, etc.), and any other sample potentially containing a substance that is harmful to the user. In variations, the consumable sample can have a volume of between 1 and 7 mL prior to processing within the sample processing chamber 110; however, the consumable sample can alternatively have any other suitable volume.

The test container 105 can be configured to couple to an analysis device (e.g., to cooperatively form an aligned system). In a specific example, the aligned system of the test container 105 coupled to the analysis device 205 can be characterized by a length less than 4 inches (e.g., a length of 3.5 inches), a width less than 1.5 inches (e.g., a width of 1.0 inches), and a height less than 3.5 inches (e.g., a height of 3.1 inches). In this specific example, the analysis device can possess substantially similar dimensions. In another specific example, the test container can be defined by a height less than 3 inches (e.g., a height of 2.5 inches). However, any suitable component of the system 100 can possess any suitable dimensions.

Components of the system 100 can be assembled and/or coupled (e.g., coupling between the test container 105 and the analysis device 205, coupling between components of the test container 105, coupling between components of the analysis device 205, etc.) using sealants, press fitting, interference fits, tongue-and-groove interfaces, threaded interfaces, adhesives, ultrasonic welding, clips, and/or any other suitable mechanism.

In variations where the test container 105 can couple with the analysis device 205 in an alignment configuration 211 of an aligned system, the system 100 preferably operates when the system 100 is stood up on the base of the analysis device 205 (e.g., with the base physically against a non-system surface such as a table; with the base arranged at a non-zero angle to a gravity vector; etc.), as opposed to if the system 100 is lying on its face (e.g., a triangular face physically connected to the base of the analysis device 205; with the base arranged substantially parallel a gravity vector; etc.). Additionally or alternatively, the system 100 is operable in any orientation in the alignment configuration 211.

In relation to a weight of the system 100, components of the system 100 can have any suitable weight. In a specific example, the analysis device can possess a weight less than 2.5 oz, and the test container can possess a weight less than 0.85 oz, but any suitable component can have any suitable weight characteristic. Regarding materials of the system 100, components of the system 100 can be constructed with materials including: glass, metal, ceramic, plastic, or any other suitable material or combination thereof. In a specific example, components of the system 100 can be constructed using double shot plastics to enable durability.

In a variation, components of the system 100 can be waterproof and/or water-resistant. In an example, components of the system 100 with surfaces exposed to interaction with a consumable sample can be coated with a water-repellant coating. In another example, the system 100 can include waterproofing sealants such as gaskets, o-rings, and/or other suitable waterproofing components. In a specific example, the test container 105 can include a waterproofing sealant arranged at the first chamber 111 along the circumference of the consumable reception opening 112, such that waterproofing sealant can act as a sealing intermediary between the first chamber in and the driving element 120 in response to coupling of the a first chamber 111 and the driving element 120 by the user. Additionally or alternatively, components of the system 100 can maintain functionality upon exposure of different components of the system to different types of consumable samples (e.g., of varying viscosity, chemicals, liquid, solid, gas, etc.). However, the system 100 can include any suitable waterproofing element and components of the system 100 can have any suitable resilience.

However, the system 100 can possess any suitable mechanical characteristic.

3.1 System—Test Container

Figure 2A:
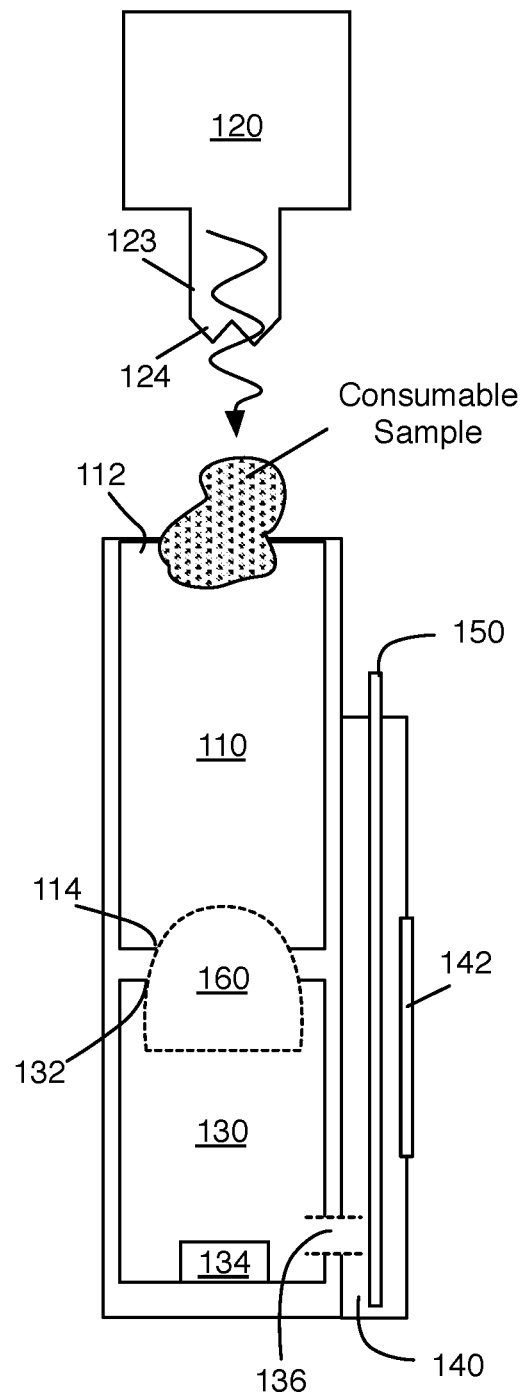
FIGS. 2A and 2B depict embodiments and variations of a portion of a system for detection of harmful substances.

As noted above and shown in FIGS. 1 and 2A-2B, in an embodiment, the test container 105 includes: a sample processing chamber 110 and a detection substrate 150. In variations, the test container 105 can additionally or alternatively include: first chamber in, a second chamber 112, an analysis chamber 115, and a detection window 117. The test container 105 can additionally or alternatively include any suitable components.

The test container 105 functions to receive the consumable sample, generate a homogenized sample upon processing of the consumable sample, combine the homogenized sample with a process reagent to produce a dispersion, expose the dispersion to the detection substrate 150, and provide optical access to the detection substrate for use and analysis by an associated analysis device 205.

In variations, the test container 105 can be a test container as described in U.S. patent application Ser. No. 15/265,171 filed on 14 Sep. 2016, the entirety of which is incorporated herein by this reference and hereinafter referred to as U.S. application Ser. No. '171. However, the test container 105 may be any other suitable test container having some or all of the features described in detail below, and the test container 105 and/or components of the test container 105 can possess any suitable characteristics.

3.1.A Test Container—Sample Processing Chamber

The sample processing chamber no functions to receive and facilitate processing of a consumable sample that the user intends to analyze for presence of a harmful substance (e.g., an allergen). The sample processing chamber 110 preferably includes an analysis chamber 115, which contains the detection substrate 150 and which preferably includes a transparent detection window 117 that provides optical access to the detection substrate 150. The sample processing chamber no can also include: a first chamber 111 that functions to receive the consumable sample and in which the consumable sample is ground (e.g., transformed from an inhomogeneous consumable sample to a homogenized sample using a burr grinder), and a second chamber 112 into which the homogenized sample is transferred, and in which the homogenized sample is mixed with one or more process reagents to form a dispersion that is brought into contact with the detection substrate 150 for detection of the substance.

The sample processing chamber no preferably defines a consumable sample fluid path through each of the first, second, and analysis chambers of the test container 105 between the consumable reception opening 112 and the detection substrate. The consumable sample can preferably be characterized by different phases (e.g., solid phase, liquid phase, gaseous phase) throughout the sample fluid path. For example, a solid consumable sample can be received at an opening of the sample processing chamber. Upon grinding of the solid consumable sample into a homogenized sample, and mixing of the homogenized consumable sample with at least one process reagent, the consumable sample is preferably in a liquid dispersion phase for transfer to a detection substrate 150. However, the consumable sample can have any suitable phase along the sample fluid path. Consumable sample and/or other fluid flow through the sample fluid path can be gravitationally driven, magnetically driven, capillary driven, hydrostatically driven, pressure driven, and/or driven through any suitable mechanism. However, the sample and/or the sample fluid path can have any suitable flow characteristics at any point along the consumable sample path.

The sample processing chamber preferably receives a consumable sample by way of a consumable reception opening substantially as described in U.S. application Ser. No. '171, incorporated above, but can additionally or alternatively receive the consumable sample in any suitable manner.

In variations including a first chamber 111 and second chamber 112, the first and second chamber are preferably configured substantially as described in U.S. application Ser. No. '171, incorporated above, but can additionally or alternatively be configured to augment processing of the consumable sample in any suitable manner. The processing and transfer of the consumable sample in and between each of the subchambers of the sample processing chamber no (e.g., the first chamber 111, the second chamber 112, the analysis chamber 115) is preferably performed substantially as described in U.S. application Ser. No. '171, but can additionally or alternatively be performed in any suitable manner and using any suitable components, as described in U.S. application Ser. No. '171 or otherwise.

Figure 4:
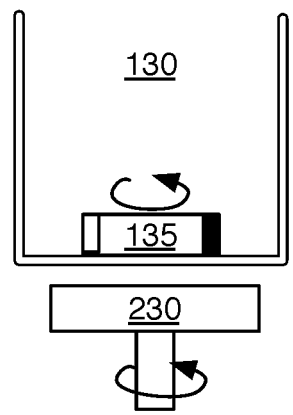
FIG. 4 depicts an example of a portion of a system for detection of harmful substances.

In some variations, the sample processing chamber no and/or subchamber(s) thereof (e.g., the second chamber 112) can include a mixing element 1101 that functions to facilitate mixing of the homogenized sample with a process reagent within the sample processing chamber no. The mixing element 1101 can be disposed within the second chamber 112, and/or can be coupled to the sample processing chamber no in any other suitable manner. The mixing element 1101 is preferably configured to cooperate with a mixing module 230 of an analysis device 205, as described in further detail below, such that the mixing element 1101 and the mixing module 230 complement each other to provide a mixing mechanism within the second chamber 112; however, variations of the system 100 can entirely omit the mixing element 1101 and/or the mixing module 230 and facilitate combination of the homogenized sample with the process reagent in any other suitable manner (e.g., the process reagent can be combined with the consumable sample during processing within the first chamber 111). In variations, the mixing element 1101 can provide any one of: a magnetically-driven mechanism of mixing, an ultrasonic mechanism of mixing, a vibration-based mechanism of mixing (e.g., mechanically driven, acoustically driven), a rocking motion, a spinning-based mechanism of mixing (e.g., by forming a vortex), a shaking-based mechanism of mixing, and any other suitable mechanism of mixing. In an example, as shown in FIG. 4, the mixing element 1101 includes a magnet 135 (e.g., magnetic stir bar) configured within the second chamber 112 that is configured to magnetically couple to a complementary magnet of a mixing module 230. In the example, the complementary magnet can be coupled to a spinning motor, thereby producing rotation at the magnet 135 within the second chamber 112. In variations of the example, the magnet 135 can include a permanent magnet and/or an electromagnet. Furthermore, the magnet 135 can be a distinct element within the second chamber 112, or can additionally or alternatively be coupled to or integrated with a diaphragm 160 configured to access the second chamber 112, as described below. Furthermore, variations of the example can include any suitable number of magnets 135 of the second chamber 112.

In variations, the second chamber 112 can be prepackaged with the process reagent (e.g., where the second chamber 112 houses a processing reagent), such that the homogenized sample is automatically brought into contact with the process reagent upon transmission between the first chamber 111 and the second chamber 112. Additionally or alternatively, the second chamber 112 and/or any other suitable portion of the test container 105 can include or be coupled to a fluid delivery module (e.g., of the analysis device 205, of the test container 105, etc.) for reception of the process reagent and combination of the process reagent with the homogenized sample or the consumable sample. For instance, the process reagent can be delivered from a module integrated with one or more portions of the driving element 120 (e.g., from the plunger 128, from beneath the grinder 122), such that the process reagent does not originate from within the second chamber 112. As such, mixing of the consumable sample with a process reagent can occur prior to grinding of the consumable sample by a driving element 120.

The process reagent preferably includes an extraction solution configured to extract at least one analyte, associated with a harmful substance, from the homogenized sample, that can be detected at a detection substrate and used to indicate presence of the harmful substance. In an example for gluten detection, the extraction solution can contain 2-mercaptoethanol, or tris(2-carboxyethyl)phosphine, which operates by reducing disulfide prolamin crosslinking in a sample, and solubilizes proteins in the sample to facilitate detection. The extraction solution can additionally or alternatively contain guanidine hydrochloride, or N-lauroylsarcosine, or other disaggregating agents. In variations for other allergens, the extraction solution can include ethanol for a dairy-derived allergen (e.g., lactose), a parvalbumin extraction solution for a fish-derived allergen, an ara-h2 extraction solution for a nut derived allergen, an egg protein extraction solution for an egg-derived allergen (e.g., ovomucoid protein, ovalbumin protein, ovotransferrin protein, lysozyme protein), a tropomyosin extraction solution for a shellfish-derived allergen, and/or any other suitable extraction solution for any other harmful substance. Furthermore, variations of the process reagent(s) can additionally or alternatively include any one or more of: a reagent for lysing of a sample, a reagent for solubilization of a sample, a reagent for buffering of a sample, a reagent for dilution of a sample, and any other suitable reagent(s). For instance, in some variations, extraction and dilution of a sample to generate a dispersion can involve a first process reagent for extraction (e.g., an alcohol-based solution for extraction of gluten), and a second process reagent for dilution of a sample processed with the first process reagent, such that the dispersion has appropriate characteristics for assessment at a detection substrate 150.

In variations, the second chamber 112 can be prepackaged (e.g., prior to receipt of a consumable sample through the consumable reception opening 112) with one or more mixing elements 134 (e.g., magnets, etc.), in order to facilitate mixing of processing reagent and the consumable sample upon receipt of the consumable sample in the second chamber 112. The one or more mixing elements 134 can be prepackaged with or separated from processing reagent and/or other suitable components. However, the second chamber can house any suitable components prior to, during, and/or after receipt of the consumable sample at any suitable component of the test container 105.

Figure 2B:
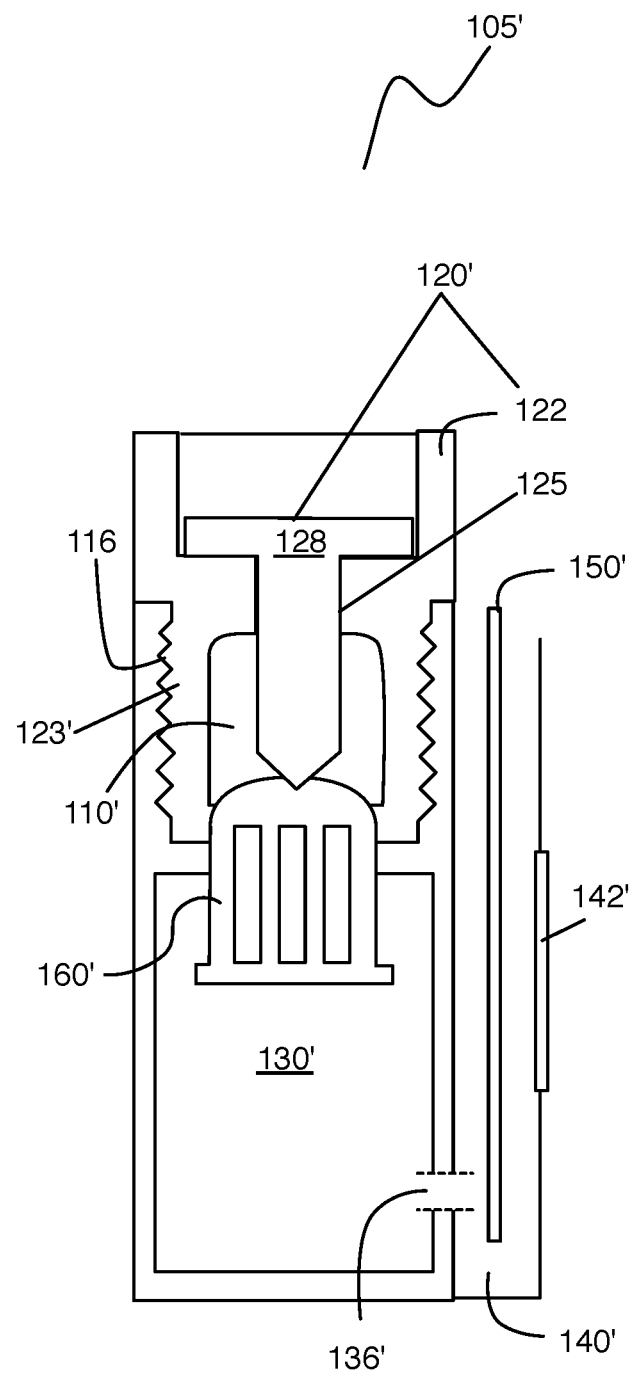
Figure 3A:
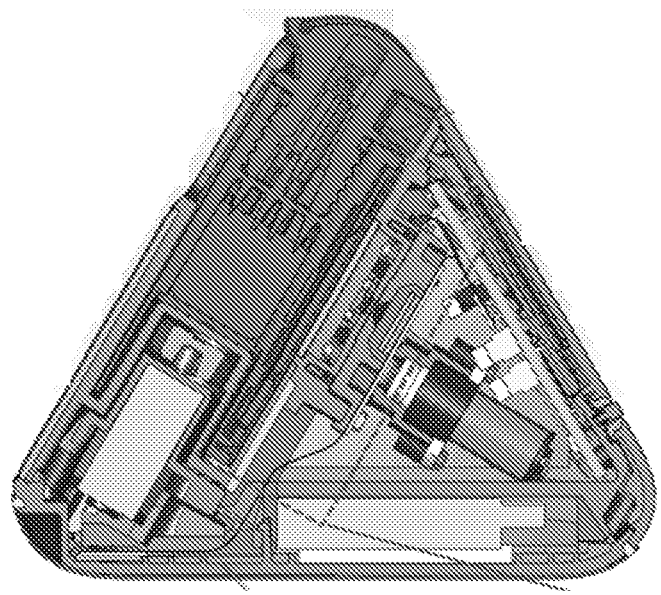
FIGS. 3A and 3B depict cross sectional views of an example of a portion of a system for detection of harmful substances.
Figure 3B:
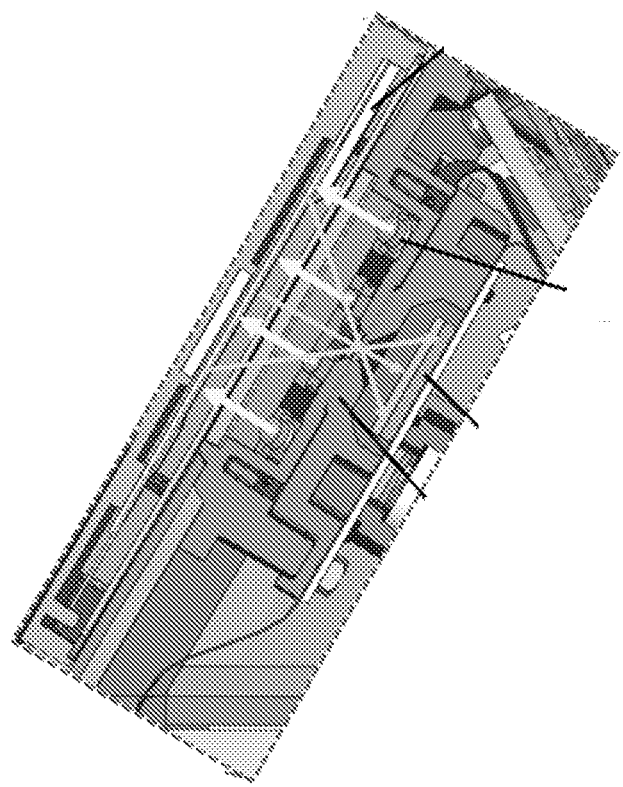

The outlet port 136 functions to facilitate delivery of a controlled volume (and/or rate of flow) of the dispersion, from the second chamber 112, to an analysis chamber 115 for detection of the harmful substance(s) within the consumable sample. The outlet port 136 is preferably situated at an inferior portion of the second chamber, an example of which is shown in FIG. 2B, in order to facilitate delivery of the dispersion from the second chamber at least in part by gravity. However, the outlet port 136 can alternatively be configured at any suitable location relative to the second chamber. The outlet port 136 preferably allows a volume of the dispersion to be transmitted to a detection substrate 150 at an analysis chamber 115 in communication with the port, wherein the volume of the dispersion is configured so as to provide an adequate amount of the dispersion without flooding the detection substrate. In a specific example, an outlet port 136 of the second chamber 112 can be sized to be impermeable to residual particles resulting from the breaking of a frangible region 161 of the diaphragm 160 when the diaphragm is detachably coupled to the interior wall of the test container body. However, the outlet port can have any suitable dimensions.

Figures 5A, 5B:
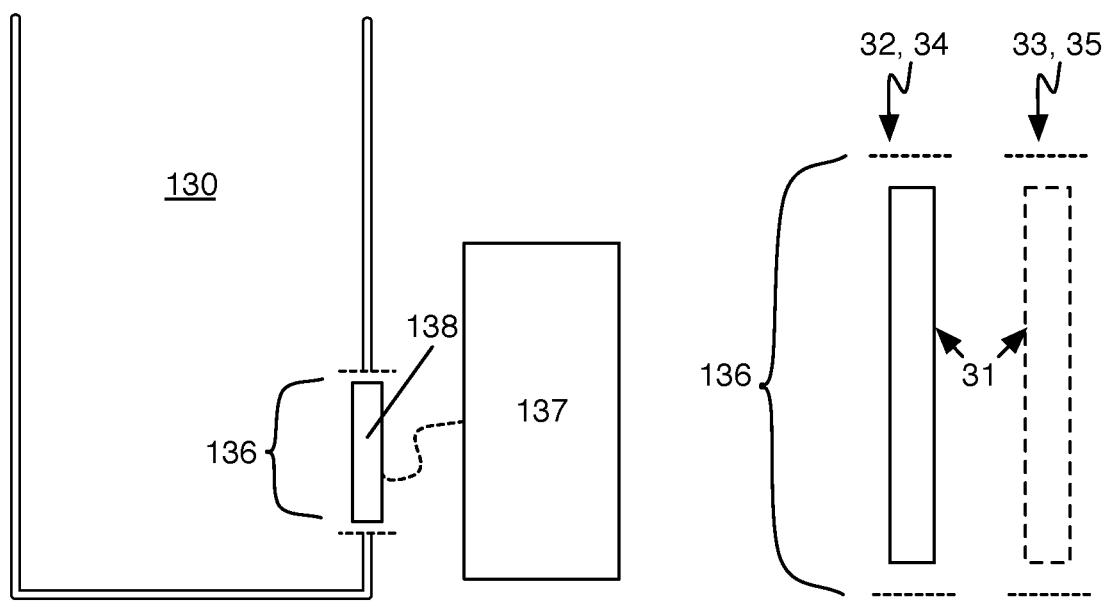
FIGS. 5A and 5B depict variations of a valve mechanism in an embodiment of a system for detection of harmful substances.
Figure 6A:
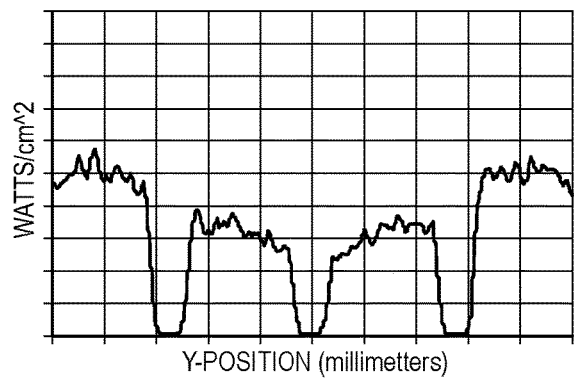
FIGS. 6A-C depict example distributions of scattered light at a variation of a detector of an example optical sensing subsystem of an embodiment of a system for detection of harmful substances.
Figure 6B:
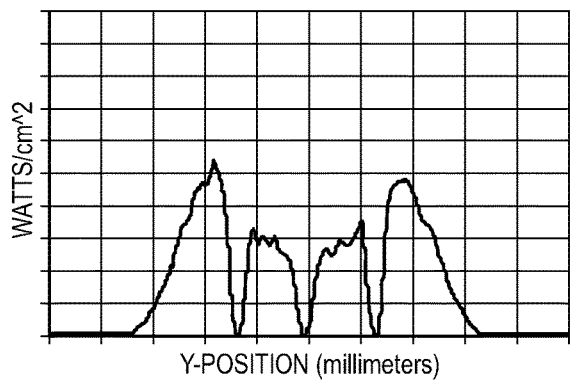
Figure 6C:
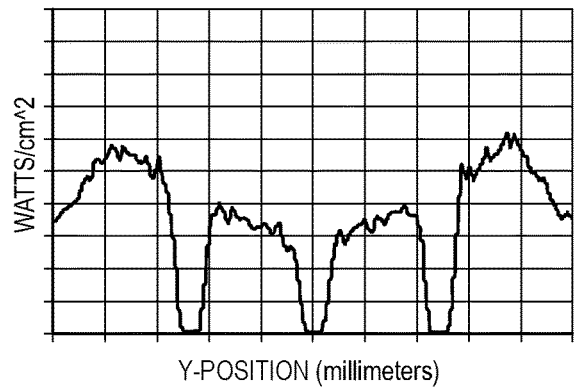
Figure 7:
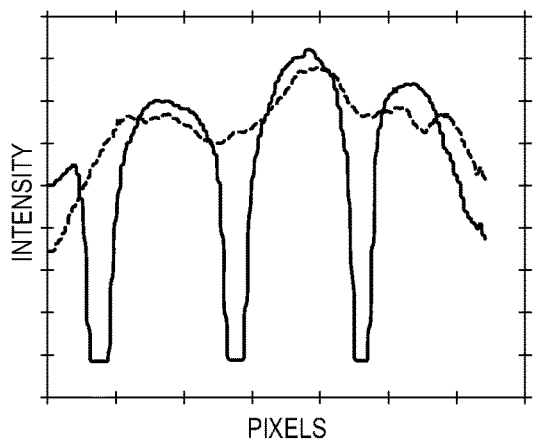
FIG. 7 depicts example image intensity data included in embodiments of systems and/or methods for detection of harmful substances.
Figure 7:
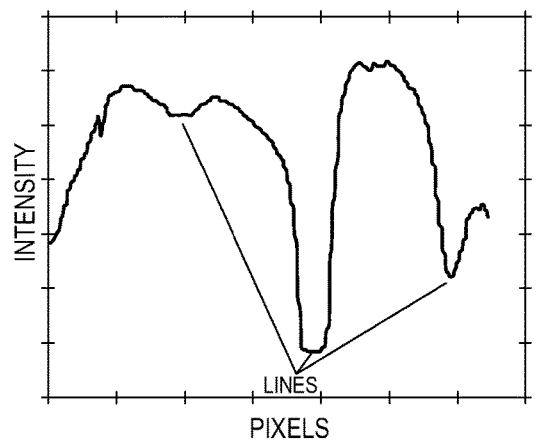
Figure 21:
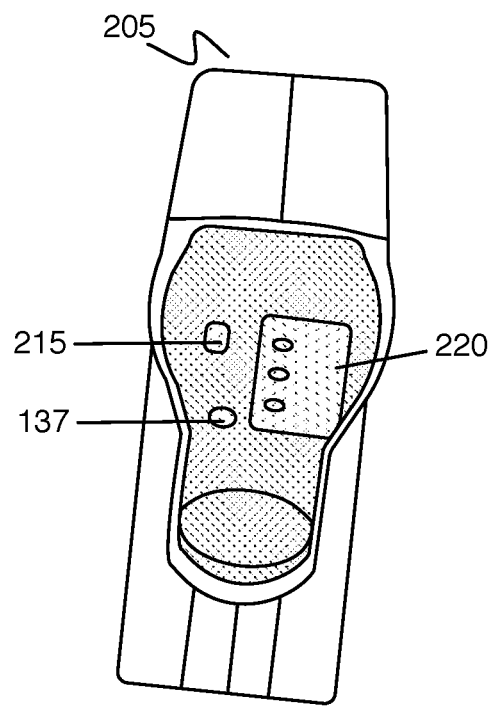
FIG. 21 depicts a variation of an analysis module for detection of harmful substances.

While the outlet port 136 can be configured to passively facilitate delivery of the dispersion to a detection substrate at the analysis chamber 115, variations of the system 100, as shown in FIGS. 5A and 21, can include an actuation system 137 configured to provide or meter a controlled volume of the dispersion to the analysis chamber 115. In one variation, an actuation system 137 coupled to the outlet port 136 can include a valve 138 that can be controllably opened and/or closed in order to dispense the dispersion into the analysis chamber 115 with a controlled volume and/or at a controlled time point. In an example, the valve 138 can include a rod 31 (e.g., needle) that is biased to be closed in a first valve configuration 32 and configured to open in a second valve configuration 33, wherein transitioning between the first valve configuration 32 and the second valve configuration 33 can be controlled by actuators (e.g., solenoids, etc.) of the test container 105 and/or analysis device 205, pressurization of the test container 105 (e.g., using a pneumatic mechanism), and/or in any other suitable manner. In the example, the rod can be biased closed using a compression spring (or other elastomeric element), and configured to transition between the first valve configuration 32 and the second valve configuration 33 upon user input (e.g., by pushing a button on the test container or the analysis device, by inputting a command at a user interface, etc.) and/or automatically (e.g., controlled by a controller of the system 100).

In another example, the outlet port 136 can include a material valve 138 configured to transition from a first state 34 to a second state 35 (e.g., reversibly, irreversibly), thereby allowing a volume of the dispersion to pass through the outlet port 136 in a controlled manner. In variations of this example, the material of the valve 138 can include any one or more of: a material (e.g., salt, sugar, polyvinyl alcohol, etc.) configured to transition from a solid state to a dissolved state (e.g., dissolvable salt wall, dissolvable in a manner that does not affect detection of an analyte at the detection substrate), a wax configured to transition from a solid state to a melted state, a material (e.g., foil, metals, plastics, etc.) configured to transition from an unpunctured state to a punctured state, and/or any other material configured to transition between states without affecting test results (e.g., without interfering with the delivery of a volume of a dispersion to a detection substrate, etc.). The transition between a first material valve configuration (e.g., closed) to a second material valve configuration (e.g., open, facilitating delivery of a volume of the dispersion) is preferably controlled by a component (e.g., a mechanical actuator, a heating element, a fluid dispersion module dispersing fluid for dissolving the material valve, etc.) of the analysis device 205. In a specific example, the analysis device 205 can include a valve motor coupled to a valve plunger that manipulates a rake to pierce with a seal of the outlet port 136 in order to open the valve hole and transition the outlet port from a first to a second configuration. However, valve-controlling components of the analysis device 205 can apply any suitable force, movement, and/or action in opening and/or closing pathways through the outlet port 136. However, the transition from the first to the second valve configuration can also be controlled by components of the test container 105, actions by the user, and/or any through any other suitable mechanism.

In another example, the outlet port 136 can be characterized by varying levels of permeability to the consumable sample, homogenized sample, liquid dispersion, components of the test container 105 (e.g., diaphragm 160, residual pieces from a broken frangible region of the diaphragm 160, etc.), and/or other suitable materials of the test container top 106 and/or sample, depending on the configuration state (e.g., between an open and a closed configuration) of the outlet port 136. In a specific example where the second chamber 112 includes an outlet port 136 including a valve 138, the analysis device 205 can include a valve motor that controls the valve 138 of the outlet port 136 to operate between: a closed position where the outlet port 136 is impermeable to flow of the consumable sample through the outlet port 136, and an open position wherein the outlet port 136 is permeable to the flow of the consumable sample through the outlet port 136, and impermeable to movement of the magnetic diaphragm 160' through the outlet port 136. In specific examples, the outlet port can include flow passage features to enable and or prevent flow of sample and/or other components. The outlet port can define protrusions, standoffs, biofilms, fluid blocking agents, damming agents, features affecting fluid dynamics, standoffs, and/or any other suitable features affecting sample flow through the outlet port 136. In an illustration, the outlet port 136 can include a flow regulator (e.g., a foam dam) to regulate the flow of the dispersion and/or other suitable component to the detection substrate 150. The flow regulator is preferably arranged at an interface between the outlet port 136 and the detection substrate 150, but can be otherwise positioned in relation to the outlet port 136. The flow regulator can preferably retain a specific volume of the dispersion and/or facilitate the delivery of a specific volume of the dispersion to the analysis chamber 115. However, the outlet port 136 can possess and/or be defined by any suitable flow passage characteristics.

Figure 19:
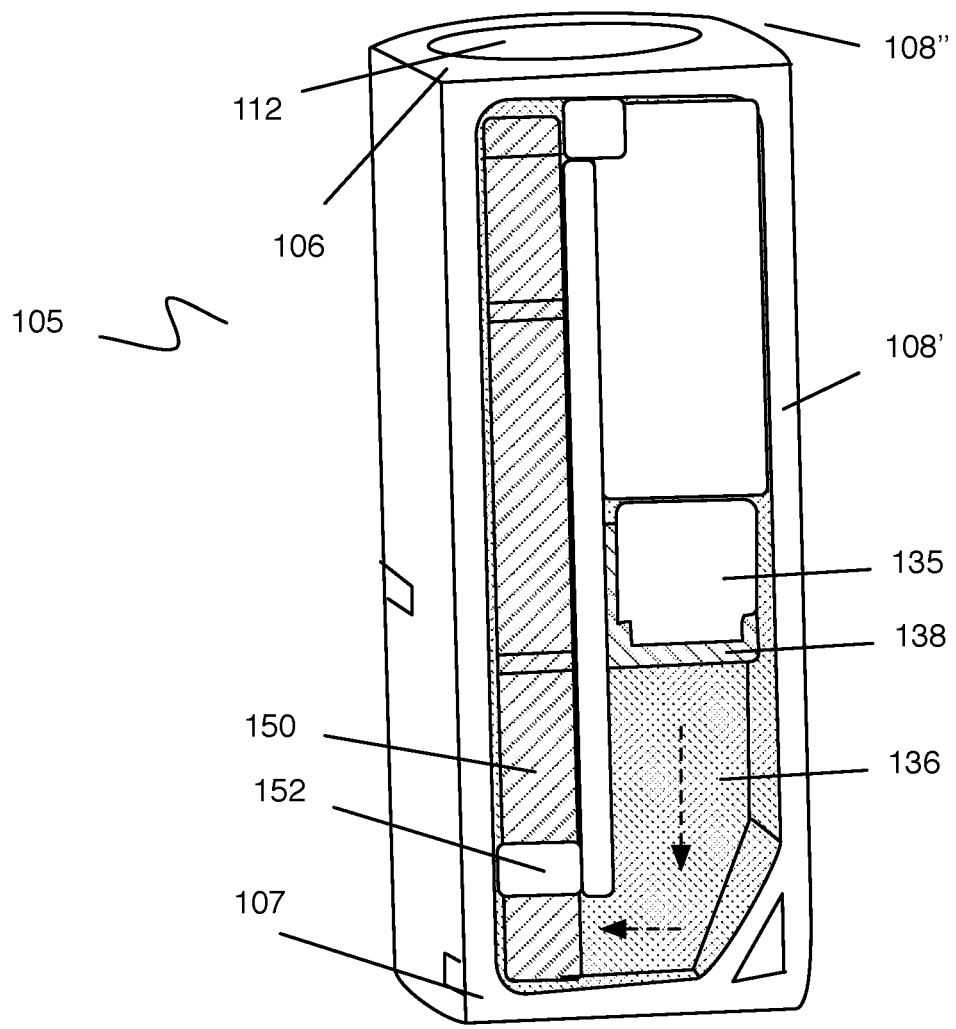
FIG. 19 depicts a variation of a system for detection of harmful substances.

In another example, the outlet port 136 can define (e.g., along with a first chamber in, a second chamber 112, an analysis chamber 115, etc.) a sample fluid path through which a consumable sample would travel during operation of the test container 105 with the analysis device 205 in the alignment configuration 211. The outlet port 136 can be appropriately dimensioned to define a specific fluid path. As shown in FIG. 19, for example, the outlet port 136, can be defined by test container body interior walls that are straight, angled, curved, and/or with any suitable orientation to define a corresponding sample fluid path. In a specific example, the outlet port 136 of the second chamber 110 can define a sample fluid path extending along a lateral axis of the test container body, but can otherwise define sample fluid paths along any suitable reference feature (e.g., any suitable axis, plane, angle, etc.) of the test container body. In specific examples, the outlet port 136 can define microfluidic pathways configured to transfer the consumable sample from the second chamber 112 to one or more suitable components (e.g., an analysis chamber 115, a chamber for further processing, etc.). However, the outlet port can be otherwise configured for defining a sample fluid path.

In another example, the outlet port 136 can be appropriately dimensioned (e.g., based upon the viscosity of the dispersion) to allow the controlled volume of the dispersion to pass into the analysis chamber 115. In variations of this example, positive pressure and/or negative pressure can also be used to drive the dispersion out of the port and into the analysis chamber.

In still another example, the outlet port 136 can include a valve 138 (e.g., a membrane, a film) that can be punctured or otherwise compromised to allow a volume of the dispersion to pass through the outlet port 136 and into the analysis chamber 115. In this example, the valve 138 could be compromised using a needle coupled to a portion of the second chamber, wherein the needle could be deflected (e.g., by a portion of the analysis device 205, in combination with spring-loading of the needle) in a manner that prevents accidental deflection by a user or other entity in contact with the test container 105. As such, the actuation system 137 can operate as a release mechanism that allows the dispersion to be conducted to a detection substrate at the analysis chamber 115. The outlet port 136 and/or actuation system 137 can, however, be configured in any other suitable manner and/or include any other suitable elements that enhance detection at a detection substrate. For instance, one variation of the outlet port 136 can include a filter proximal the port that prevents material (e.g., material that could adversely affect detection) from passing into the analysis chamber 115 and/or from reaching the detection substrate 150.

However, the second chamber 112 and/or components of the second chamber 112 can be configured in any suitable manner.

The analysis chamber 115 functions to position a detection substrate 150 proximal the outlet port 136 of the second chamber, such that the detection substrate 150 can absorb a volume of the dispersion and provide indication of presence of at least one harmful substance within the consumable sample. The analysis chamber 115 is preferably coupled to at least one of the second chamber 112 and the first chamber, and in one variation, the analysis chamber 115 is configured external to the second chamber 112, with access between the second chamber 112 and the analysis chamber 115 provided by the outlet port 136 of the second chamber 112. In an example of this variation, the analysis chamber 115 can include a slot longitudinally spanning a portion of the test container 105, as shown in FIG. 2B, wherein the slot is configured to position the detection substrate 150 proximal the outlet port 136. Portions of the analysis chamber 115 and/or components of the analysis chamber 115 (e.g., detection substrate 150) are preferably aligned, adjacent, and/or proximal along a lateral axis of the first chamber 111 and/or second chamber 112, but can be in any suitable configuration with any suitable component. However, the analysis chamber 115 can alternatively be configured in any other suitable manner.

3.1.B Test Container—Detection Substrate

The detection substrate 150 functions to indicate presence of an analyte, associated with a harmful substance, and in variations, can indicate presence based upon one or more of: a color change, fluorescence emission, infrared emission, magnetic response, electrical response, acoustic change, and any other suitable mechanism of indication. The detection substrate 150 is preferably a permeable substrate (e.g., test strip) that soaks up a portion of the dispersion and facilitates binding of one or more analytes in the dispersion with complementary antibodies (e.g., antibodies bound to cellulose nanobeads) at the detection substrate 150, to provide indication of presence of harmful substances associated with the analyte(s). The detection substrate 150 can include a single active region (e.g., a band, a line, a dot, etc.) for analyte binding, or a set of active regions for analyte binding. The active region(s) can include antibody cocktails for a single analyte associated with a harmful substance, a set of analytes associated with different harmful substances, and/or a control region configured provide a control readout (e.g., in order to enable determination of a baseline signal, in order to establish proper conductance of a test). For instance, in some variations of a detection substrate 150 with a set of active regions 151 for analyte binding, one active region can be used as a test region that is used to indicate an amount (e.g., concentration, volume, mass) of a harmful substance in a consumable sample, and another active region can be used as a control region that indicates that the test has been performed properly (i.e., such that data generated from the detection substrate 150 is reliable). The detection substrate 150 preferably includes a beginning region and an end region respectively defining the beginning and end portions of a sample fluid path through the detection substrate 150. In a specific example, the analysis chamber 115 can include a detection substrate 150 extending along a longitudinal axis of the test container body, the detection substrate 150 including a beginning region fluidly connected to the second chamber 112, and an end region proximal the first chamber in. However, the beginning and end regions of a detection substrate 150 can have any suitable positional relationship with other components of the test container 105. In some variations, the detection substrate can include multiple regions aligned along the longitudinal axis. In a specific example, the detection substrate can include, in order of fluid flow (e.g., from upstream to downstream): a test region, a hook region, and a control region. This configuration can function to detect small amounts of the target (e.g., due to the test region being first), and to determine that the sample has flowed through the majority of the detection substrate (e.g., due to the control region being last). However, the detection substrate can be otherwise configured.

In variations, a region of a detection substrate 150 can be configured to accommodate an analyte with a single binding site, or multiple binding sites (e.g., as in a sandwich assay having a first antibody that serves as a capture antibody, and a second antibody that serves as an analyte-specific antibody). However, the detection substrate 150 can additionally or alternatively include any other suitable liquid medium or sensor configured to indicate presence of a harmful substance within the consumable sample in any other suitable manner. In an example, the detection substrate 150 is a long, narrow, and flat strip of a fibrous material with regions (e.g., bands, lines, spots) of complementary antibodies to an analyte associated with a harmful substance, whereby capillary soaking of the detection substrate 150 distributes the dispersion across the detection substrate 150. In a version of the example for gluten testing, the detection substrate 150 includes a control band and a test band, having a distribution of a G12 antibody, bound to cellulose nanobeads, which is configured to bind to the 33-mer peptide of the alpha-gliadin molecule in gluten.

In a variation, the analysis chamber 115 can include a detection substrate 150 including microfluidic pathways, including channels on a patterned-paper, lab-on-a-disc, lab-on-a-chip, and/or any other suitable microfluidic devices facilitating detection of target substances in the consumable sample. Additionally or alternatively, the analysis chamber 115 and/or detection substrate 150 can include any suitable elements described in U.S. application Ser. No. 15/065,198, filed 9 Mar. 2016, which is herein incorporated in its entirety by this reference.

In some variations, the analysis chamber 115 can include a detection window 117 that enables detection of presence of a harmful substance at the detection substrate 150. As such, the detection substrate 150 can be configured to align with the detection window, such that indicators (e.g., one or more lines generated during binding of analyte at the detection substrate) can be observed through the detection window 117. The detection window 117 can substantially span an entirety of the detection substrate, or can alternatively be configured to selectively provide observation of one or more regions of interest of a detection substrate 150. The detection window can optionally function as and/or provide reference point(s) for image analysis, wherein all or a portion of the detection window is imaged with the detection substrate. The detection window 117 can be defined by an opening through the analysis chamber 115, and can additionally or alternatively include a covering (e.g., transparent covering, translucent covering) that enables observation of the detection substrate 150. Alternatively, the detection window can be a unitary piece with the test container housing, wherein the housing is made of a clear material and can optionally be selectively masked to prevent light contamination or for other purposes. In variations, the detection window 117 can further function to indicate potential defectiveness of a test container 105, detection substrate 150, and/or any other suitable portion of the system 100 in providing reliable results. For instance, in some variations, wherein detection substrates are sensitive to heat and/or humidity, the detection window 117 can be configured to indicate subjection of a detection substrate 150 to high temperatures (e.g., above 40° C.) and/or humid environments (e.g., by producing a color change in the detection window, by having the detection window fog up, etc.). Additionally or alternatively, the test container 105 can be coupled with a dessicant to prevent humidity-induced damage, and furthermore, variations of the detection window 117 can additionally or alternatively provide any other suitable function that provides information regarding potential defectiveness of a test performed using the detection substrate 150, defectiveness in analyte detection, and/or any other suitable function. For instance, the detection window 117 can provide optical qualities that provide desired properties upon illumination in order to enhance analysis of a detection substrate 150. Variations of the analysis chamber 115 can, however, entirely omit the detection window 117. For instance, a variation of the system 100 can be configured such that the detection substrate is retrieved after contacting a volume of the dispersion, and analyzed away from an analysis chamber 115 of a test container 105.

In variations with a detection window 117, the detection window 117 preferably constructed with materials and or sealants preventing liquid (e.g., dispersion, consumable sample, etc.) from unintentionally leaking from the test container 105 (e.g., onto other components of the test container 105, onto the analysis device 205). The detection window 117 is preferably coupled to the remaining test container 105 with a sealant (e.g., heat seal), but can additionally or alternatively be coupled to the test container through adhesives (e.g., UV glue), press fitting (e.g., ultrasonic), and/or any other suitable mechanism. The detection window 117 is preferably made of a rigid material (e.g., brittle plastic, plastic blend, etc.) that prevents a user from piercing the detection window 117. Additionally or alternatively, the detection window 117 can be made of a softer material and/or any other material possessing any suitable characteristic. In providing modularity, the detection window 117 can be made of multiple components and/or materials. For example, the detection window 117 can include a rigid component to prevent user penetration and a softer component to facilitate penetration by the valve plunger. However, the detection window can be assembled with any suitable materials and/or sealants.

Variations of the test container 105, as noted earlier, can be characterized by modularity in using a combination of reusable and/or non-reusable components, such that portions of the test container 105 can be reused, and other portions of the test container 105 can be disposed after a limited number of uses. For instance, in some variations, all portions of the test container 105 can be configured to be reusable, aside from the detection substrate 150/analysis chamber 115, such that the detection substrate 150 are disposed after each use, and the test container 105 can be reused for another instance of detection upon replacement of the detection substrate 150/analysis chamber. In other variations, all portions of the test container 105 can be configured to be reusable, aside from the detection substrate 150, such that the detection substrate 150 is disposed after each use, and the test container 105 can be reused for another instance of detection upon replacement of the detection substrate 150. The test container 105 can, however, provide any other suitable combination of reusable and disposable components. In providing modularity, portions of the test container 105 are preferably made of a material that is recyclable, compostable and/or processable, and in variations, can include any one or more of: a polymer (e.g., a plastic), a metal, and a glass. For example, a portion of the test container 105 can be made of a compostable material, while the detection window 117 of the test container can be made of a recyclable plastic. However, variations of the test container 105 can alternatively include any other suitable material (e.g., ceramic), and can be configured to be entirely reusable or entirely disposable.

3.1.C Test Container—Test Container Body

As shown in FIG. 19, the test container can additionally or alternatively include a test container body, which functions to provide mechanical support and/or shielding to components of the test container 105. The test container body can include a test container top 106, a test container bottom 107 opposing the test container top 106, and/or any suitable number of side walls 108 physically connecting the test container top 106 and the test container bottom 107. However, the test container body can include any suitable components in any suitable configuration.

As shown in FIG. 19, in a variation, the test container body can be keyed (e.g., possess an asymmetric profile) for insertion into the analysis device 205. This can function to facilitate reliable, repeatable test container alignment in a desired orientation within the analysis system, which can be desirable when the detection substrate is asymmetrically arranged on the test container and/or when the optical system is asymmetrically located in the analysis chamber. This profile may not be as advantageous if the detection substrate extends about the perimeter of the test chamber, or if the test container is inserted into a test lumen surrounded by optical sensors.

For example, the test container 105 can include a curved side wall 108' and a flat side wall 108". In another example, the test container body can define a test container top geometrically asymmetric from a test container bottom. In a specific example, the test container body can define a curved side 108' physically connected to the test container top 106 and the test container bottom 107, wherein the curved side is proximal the first chamber 111 and the second chamber 112 of the test container 105. In this specific example, the test container body can additionally or alternatively define a flat side 108" opposing the curved side 108' and physically connected to the test container top 106 and the test container bottom 107, wherein the flat side 108" is proximal and/or forms the analysis chamber. In another example, the test container 105 can define a cross section including a tongue, complimentary to a groove defined by the analysis device opening. However, the test container body can be configured in any suitable manner.

As a person skilled in the art will recognize from the previous detailed description and from the figures and claims, modifications and changes can be made to the embodiments of the test container 105 without departing from the scope of the test container 105.

3.2 System—Analysis Device

As noted above and shown in FIG. 1, in an embodiment, the analysis device 205 includes: a housing defining a test container lumen 210 and a component volume 222, the test container lumen configured to receive a test container 105; a mixing module 230 configured to mix the homogenized sample in the associated test container 105 with a process reagent, an optical sensing subsystem 220 mounted to the housing within the component volume and configured to enable detection of presence of the harmful substance at the detection substrate 150, and a processing and control system 240 configured to receive and process signals from the optical sensing subsystem 220, thereby producing an output indicative of presence of the harmful substance in the consumable sample.

3.2.A Analysis Device—Test Container Lumen

The test container lumen 210 functions to receive the test container 105, and can additionally function to align the test container 105 to facilitate detection of analytes at a detection substrate, in cooperation with the optical sensing subsystem 220. The test container lumen 210 preferably defines a test container opening sized to receive the test container 105. As such, the test container lumen 210 preferably mates with the test container 105 (e.g., an external morphology of the test container 105), in a consistent manner, such that the test container 105 can only be positioned within the test container lumen 210 of the analysis device in one of a discrete set of orientations (e.g., in variations wherein the test container 105 has an orientation). In a specific example, the test container lumen can be geometrically complementary to the test container 205, where the test container lumen 210 can include a superior portion geometrically complimentary to a test container top 106, and an inferior portion geometrically complimentary to a test container bottom 107. Alternatively, in variations wherein the test container 105 is symmetric (e.g., having a rotational axis of symmetry), the test container lumen 210 can be configured to accommodate symmetry in the test container 105 in relation to positioning the test container 105 relative to other elements of the analysis device 205 (e.g., the optical sensing subsystem 220, the mixing module, 230). While the test container lumen 210 can receive a test container 105 into an interior portion of the analysis device 205, test container lumen 210 can additionally or alternatively be configured to couple the test container 105 to an external portion of the analysis device 205. For instance, the test container lumen 210 can include a mechanism (e.g., latch, slide, magnet) configured to couple the test container 105 to at least a portion of the exterior of the analysis device 205.

In variations where the analysis device 205 defines a base 206 and a triangular face 207, the test container opening of the test container lumen 210 can be proximal an apex 208 of the triangular face 207. Further, a longitudinal axis of the test container lumen 210 can be substantially parallel a side of the triangular face 207 and/or angled with respect to the base 206 (e.g., perpendicular the base). Additionally or alternatively, a lateral axis of the test container lumen can intersect a plane of the base 206. In this variation, a test container 105 can preferably be placed at the test container opening proximal the apex 208, and the test container 105 can be guided (e.g., slid, gravitationally driven, with guiding rails, etc.) into an alignment configuration 211 with the analysis device 205. However, the test container lumen 210 can be oriented in any suitable configuration with respect to the analysis device 205 and/or test container 105.

Figure 8A:
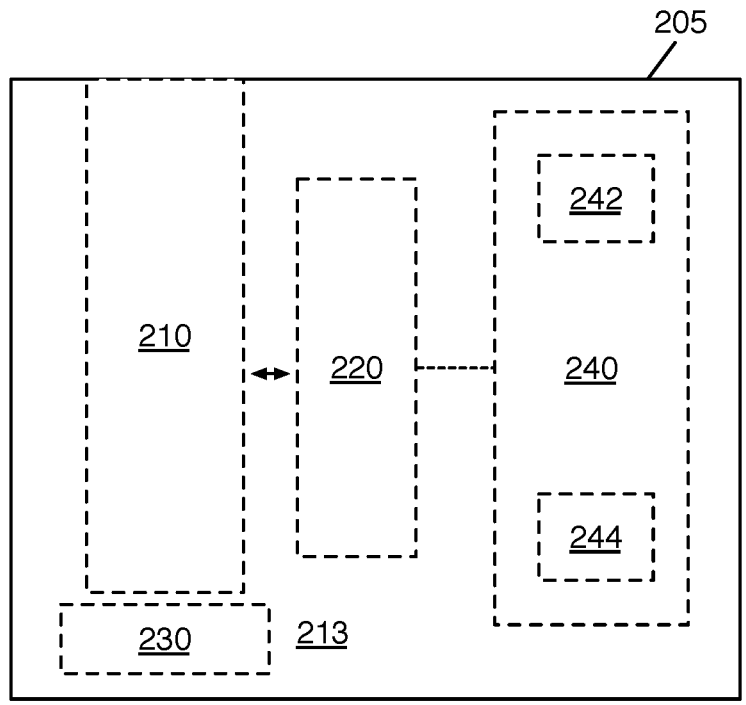
Figures 8B, 8C:
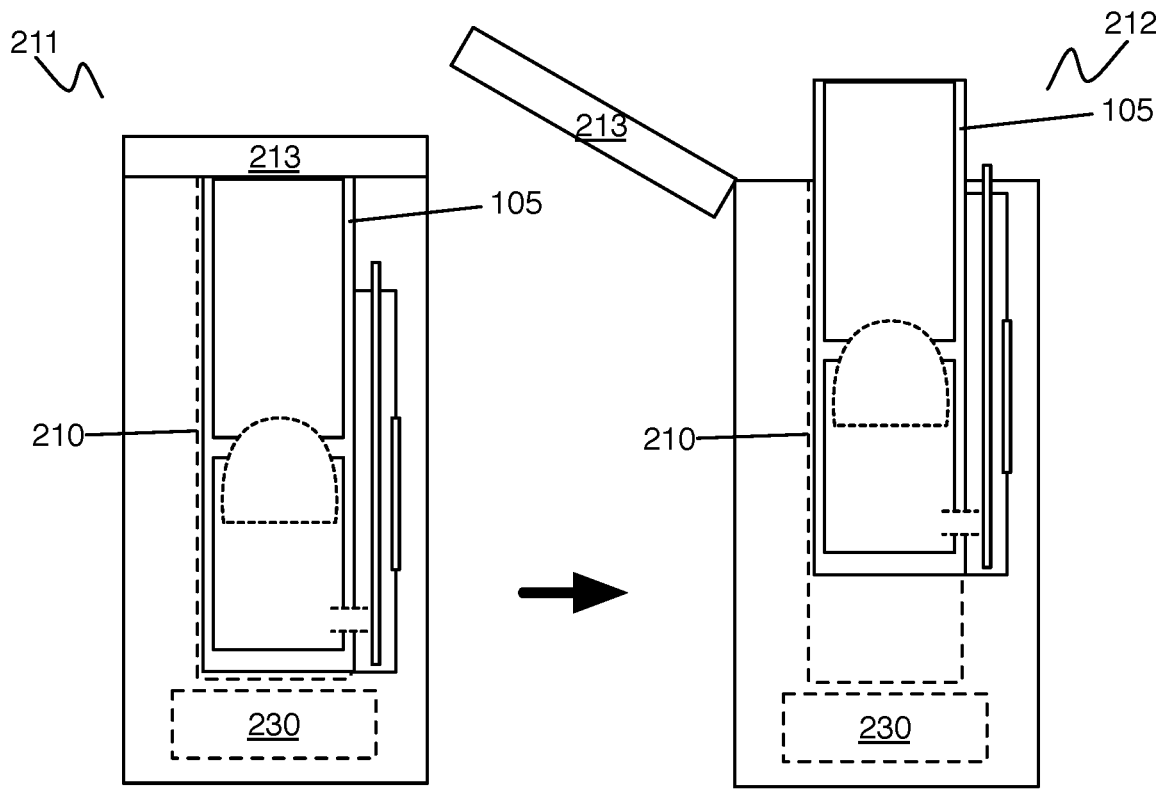

As such, in some variations, the test container lumen 210 is preferably configured to receive the test container 105 in an alignment configuration 211, and to release the test container 105 from the analysis device 205 in a releasing configuration 212 (e.g., post-analysis of a sample), as shown in FIGS. 8A-8C. In producing the alignment configuration 211, the test container lumen 210 can be coupled to a cap 213 or other mechanism (e.g., latch, tab, etc.) that facilitates retention (e.g., locking) of the test container 105 in the alignment configuration, thereby preventing undesired deviations from the alignment configuration, which could affect analysis of a detection substrate 150 of the test container 105. In variations of the test container lumen 210 with a cap 213, the cap 213 can further function to facilitate processing of a consumable sample and/or homogenized sample within the test container. For instance, in one variation, the cap 213 can include an actuating element 214 (e.g., disposed within an interior surface of the cap 213, accessible from an exterior surface of the cap 213, etc.) configured to depress a plunger 128 of the test container 105 to transition a diaphragm between the first chamber 111 and the second chamber 112 of the test container 105 between a first configuration 167 and a second configuration 168, as shown in FIGS. 8A-8E. The actuating element 214 can be magnetically driven, pneumatically driven, mechanically driven (e.g., using springs, etc.), or driven in any other suitable manner. Actuation of a plunger 128, as facilitated by the cap 213, in this variation can be automatically performed once the test container 105 is in the alignment configuration within the test container lumen 210, and/or can be triggered (e.g., by the user, by a control system of the analysis device 205) in any other suitable manner. As such, in an example workflow of this variation, a user can place a test container 105 within the test container lumen 210 of the analysis device, with the consumable sample substantially homogenized and the diaphragm 160 in the first configuration 167, and closing of the cap 213 can automatically initiate depressing of the plunger 128 to transition the diaphragm 160 into the second configuration 168 (e.g., without knowledge by the user). Then, after detection using the optical sensing subsystem 220, as described below, the cap 213 can be opened and the test container 105 can be released from the analysis device 205 in the releasing configuration. In variations, locking and unlocking of the test container 105 from the analysis device 205 can be manually triggered (e.g., by a user) through mechanical instructions (e.g., a button, switch), audio instructions (e.g., voice control, etc.), visual instructions (e.g., a hand gesture, etc.), touch instructions (e.g., tap, hold, pinch, touching of a digital user interface, pushing and/or pulling force applied to the test container 105 in the test container lumen 210, etc.), and/or through any suitable mechanism. In other variations, locking and unlocking of the test container 105 can be automatically triggered, for example, at specific points along the sample fluid path (e.g., after detection of one or more analytes with the optical sensing subsystem 220, etc.), after detection of the test container 105 in the test container lumen 210 (e.g., by a test container detection region 215 described below, etc.), and/or at any suitable time by any suitable mechanism. However, variations of the test container lumen 210 can alternatively omit a cap or other mechanism configured to retain the test container 105 in the alignment configuration.

As shown in FIG. 21, in another variation, the test container lumen 210 can include a test container detection region 215 configured to detect the receipt of the test container 105 at the test container lumen 210 in an alignment configuration 211. The test container detection region 215 preferably includes a translucent region (e.g., constructed with glass, plastic, translucent materials, etc.) adjacent a sensor (e.g., a light sensor, a motion sensor, etc.) of the test container detection region 215. The sensor is preferably configured to determine whether a test container 105 is present in the test container lumen 210 and/or whether the test container 105 is properly in an alignment configuration 211 with the analysis device 205. Additionally or alternatively, the test container detection region 215 can include any other suitable components facilitating detection of the test container top 105 at the analysis device 205.

However, the test container lumen 210 and/or components of the test container lumen 210 can be configured in any suitable fashion.

3.2.B Analysis Device—Mixing Module

Figure 20:
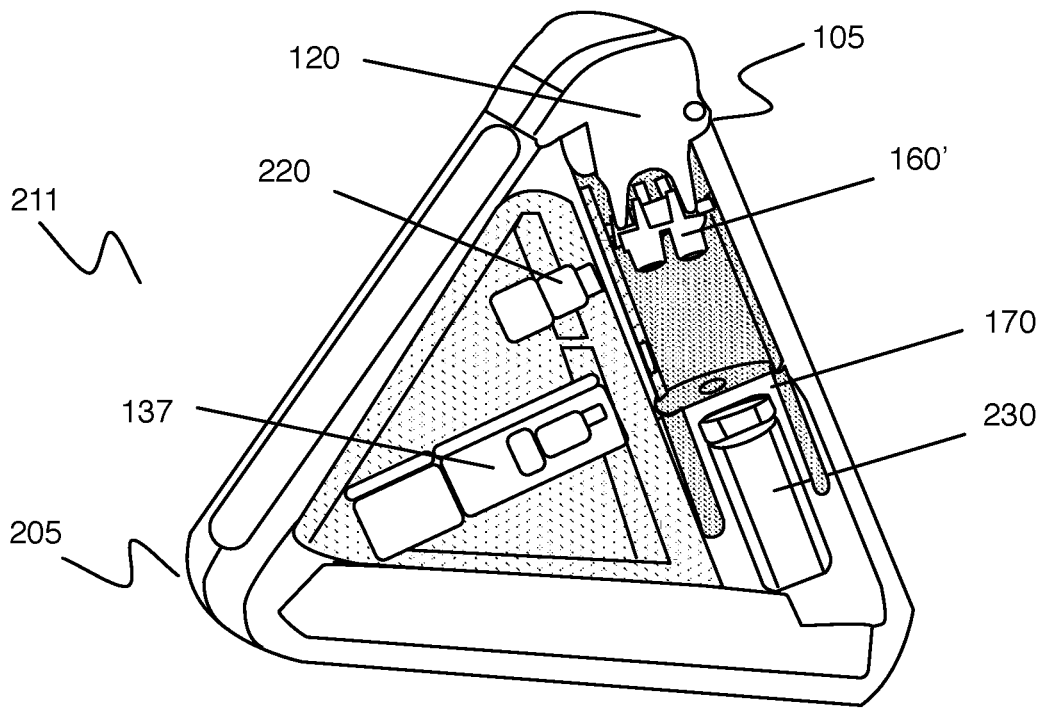
FIG. 20 depicts a variation of an analysis module for detection of harmful substances.

The mixing module 230 functions to facilitate active mixing of a homogenized sample of the test container 105 with a process reagent (e.g., extraction reagent), in order to produce a dispersion that can be delivered to a detection substrate for analysis. The mixing module 230 preferably operates in cooperation with a mixing element 1101 of the test container 105 (e.g., of a second chamber 112 of the test container), thereby forming a complementary portion of a mechanism that provides solution mixing. Thus, the mixing module 230 is preferably situated proximal to a portion of the test container 105 having the homogenized sample and the process reagent, in the alignment configuration of the test container 105. As shown in FIG. 20, when the test container 105 and analysis device 205 are in an alignment configuration 211, the mixing module 230 is preferably partially encapsulated by the motor cavity 170 of the test container 105, but can additionally or alternatively be positioned at any suitable location relative the test container 105 in the alignment configuration 211.

As noted above and shown in FIG. 4, the mixing module 230 can provide a magnetically-driven mechanism of mixing, an ultrasonic mechanism of mixing, a vibration-based mechanism of mixing (e.g., mechanically driven, acoustically driven), a rocking motion, a spinning-based mechanism of mixing (e.g., by forming a vortex), a shaking-based mechanism of mixing, and any other suitable mechanism of mixing. In an example wherein the second chamber 112 of a test container 105 includes a magnetic mixing element 1101, the mixing module 230 can include a complementary magnet situated proximal to the second chamber 112 in the alignment configuration of the system 100. In the example, the complementary magnet of the mixing module can be coupled to a spinning motor, thereby producing rotation at the magnetic mixing element 1101 within the second chamber 112. In a specific example, the mixing module 230 can be proximal the base 206 of the analysis device 205, and wherein the mixing module 230 includes a complementary magnet coupleable to the magnetic element 163 of the magnetic diaphragm 160', and a spinning motor coupled to the complementary magnet. In variations of this example, the mixing module 230 can be configured to detect proper coupling between the complementary magnet of the mixing module 230 and the magnetic mixing element 1101 within the second chamber 112 of the test container 105 (e.g., byway of sensing of a magnetic force, by way of detection of motion of the magnetic mixing element 1101 in response to motion of the complementary magnet, etc.). The mixing module 230 can, however, be configured in any other suitable manner.

The mixing module is preferably controlled by the processing system of the analysis system, but can be otherwise controlled. The mixing module can include coupling sensors, which function to determine whether the mixing module properly engaged the mixing mechanism within the test container (e.g., force sensors depressed when the motor rotor engages the test container bottom, magnetic sensors or Hall effect sensors that detect when a magnetic element within the test container is proximal and/or is moving, etc.). The mixing module can optionally include rotary encoders (e.g., which can be used to determine whether the mixing module was performing as expected), or any other suitable set of sensors. The mixing module is preferably bidirectional (e.g., operable both clockwise and counterclockwise), but can optionally be unidirectional or actuate in any other suitable manner.

In a variation, the mixing module 230 can include a mixing status sensor configured to start and/or stop mixing based on a determined mixing status of the consumable sample in the second chamber 112. One or more mixing status sensors can include a light sensor, weight sensor, phase sensor (e.g., liquid, gaseous, solid phase), etc. Additionally or alternatively, mixing by the mixing module 230 can progress for a predetermined time period (e.g., determined by a manufacturer, by a user, etc.), an automatically determined time period (e.g., based on mixing status sensor readings), and/or for any suitable period of time.

In another variation, the mixing module 230 can include an actuation motor coupled to a complementary magnet of the mixing module 230, and configured to move the complementary magnet in response to completion of mixing in order to facilitate unimpeded flow of the liquid dispersion from the second chamber 112 through the outlet port 136. For example, after completion of mixing the consumable sample with processing reagent in the second chamber 112, an actuation motor of the mixing module 230 can move the complementary magnet (e.g., along a guided rail) to a position proximal a second chamber portion opposing the outlet port 136. However, the mixing module can facilitate consumable sample flow through the outlet port 136 in any suitable manner.

However, the mixing module 230 can be configured in any suitable fashion.

3.2.C Analysis Device—Optical Sensing Subsystem

Figure 9:
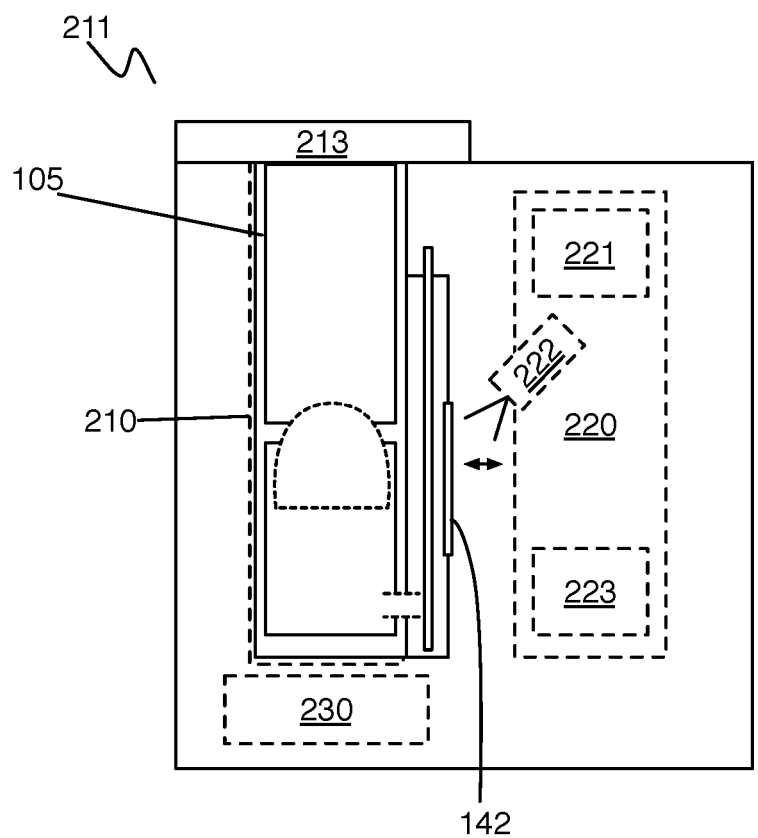
FIG. 9 depicts one variation of a portion of a system for detection of harmful substances.

As shown in FIG. 21, the optical sensing subsystem 220 functions to facilitate detection of one or more analytes, indicative of presence of a harmful substance within a consumable sample. The optical sensing subsystem 220 further functions to facilitate automated reading of a detection substrate 150, such that effects of user error are minimized; however, the optical sensing subsystem 220 can be configured to provide manual assessment of test results of a detection substrate 150. The optical sensing subsystem 220 is preferably aligned with the detection window 117 of the analysis chamber 115 of the test container 105 in the alignment configuration 211, as shown in FIG. 9, in order to provide a compact configuration and facilitate direct communication between a detection substrate and the optical sensing subsystem 220. In a specific example where the test container lumen 210 defines a first side geometrically complementary to a curved side wall 108' of the test container body, and an optical analysis side opposing the first side and geometrically complementary to a flat side wall 108" of the test container body, the optical sensing subsystem 220 can be optically aligned with the optical analysis side of the test container lumen 210. However, in other variations, the detection window 117 of the analysis chamber 115 and the optical sensing subsystem 220 can alternatively be misaligned, and configured to communicate using elements (e.g., mirrors, etc.) that facilitate indirect communication between a detection substrate 150 and the optical sensing subsystem 220. The optical sensing subsystem 220 preferably has an adequate sensitivity, resolution, and field of view in order to accurately and reliably detect signals from a detection substrate 150. In one variation, the sensitivity, resolution, and field of view cooperate to enable detection of a single analyte at a single region (e.g., dot, line, band) of a detection substrate 150 and in another variation, the sensitivity, resolution, and field of view cooperate to enable detection of multiple analytes (e.g., associated with different allergens) and/or control signals at multiple regions (e.g., dots, lines, bands) of a detection substrate 150. While one optical sensing subsystem 220 is described, the analysis device 205 can, however, include any other suitable number of optical sensors 220 to facilitate detection of one or more analytes at one or more regions of a detection substrate 150. The optical sensing subsystem also preferably includes an illuminator 221 and an imager 222, as described in detail in the following sections.

The optical sensing subsystem 220, and in particular the illuminator 221, is preferably configured to generate various distributions of radiant intensity 2211 (e.g., radiant flux) at the surface of the detection substrate. In general, the distribution(s) of radiant intensity produced by the illuminator 221 at the surface of the detection substrate is preferably configured to maximize the light scattered via diffuse scattering that reaches the detector 223 of the imager 222, and to minimize the light that reaches the detector 223 via specular reflection off of various surfaces in the vicinity of the optical pathway between the illuminator 221 and the imager 222 (e.g., the detection window 117, portions of the housing 210, etc.). Additionally or alternatively, the distribution of radiant intensity produced by the illuminator 221 can be configured to produce a substantially uniform pixel intensity distribution at the detector 223, in the presence of a substantially uniformly absorbing and/or scattering detection substrate (this can, in variations, result in a substantially non-uniform distribution of radiant intensity due to the optical transfer function between the illuminator 221, detection substrate 150, and the detector 223). However, the distribution of radiant intensity produced by the illuminator 221 can additionally or alternatively be configured in any suitable manner.

The distribution 2211 can be configured in several ways. The distribution 2211 can be configured, for example, by way of adjusting the optical power(s) emitted by the illuminator 221. For example, the power emitted by an end portion of the illuminator (e.g., LEDs located at one or both ends of an illuminator including a linear array of LEDs) can be increased relative to a center portion of the illuminator, such that the distribution 2211 has a greater radiant intensity at an end region (or end regions) of the detection window than a center region. The emitted power can be static during operation of the illuminator, or it can be modulated (e.g., the power of portions of the illuminator can be time-dependent). The distribution 2211 is preferably spatially non-uniform, and the spatial non-uniformity is preferably achieved by the physical arrangement of the illuminator relative to the detection window. For example, the illuminator can be separated from the detection window by a spacing such that light emitted by the illuminator is concentrated at a longitudinal edge of the detection window, resulting in an edge-oriented illumination of the detection substrate (specific example shown in FIGS. 23A and 23B). Multiple illuminators can be spaced apart by a distance shorter than the length of the detection window, a distance longer than the detection window, or otherwise configured. The distribution 2211 can additionally or alternatively be configured by way of occluding a portion of the emitted light in the vicinity of the illuminator 221, so as to "shadow" (e.g., block from direct illumination) portions of the detection substrate 150 and thereby reduce unwanted reflections and/or optical noise. For example, a baffle 226 (which can, in variations, be a portion of a housing of the imager 222) can extend into the optical pathway between the illuminator 221 and the detection substrate 150 such that portions of the detection substrate 150 do not receive direct illumination by the illuminator 221. In a specific example, the imager 222 is positioned to act as a baffle 226 such that a portion of the light emitted by the illuminator 221 is prevented from directly illuminating the detection substrate, and a longitudinal edge of the substrate is directly illuminated as shown in FIG. 22.

Figure 22:
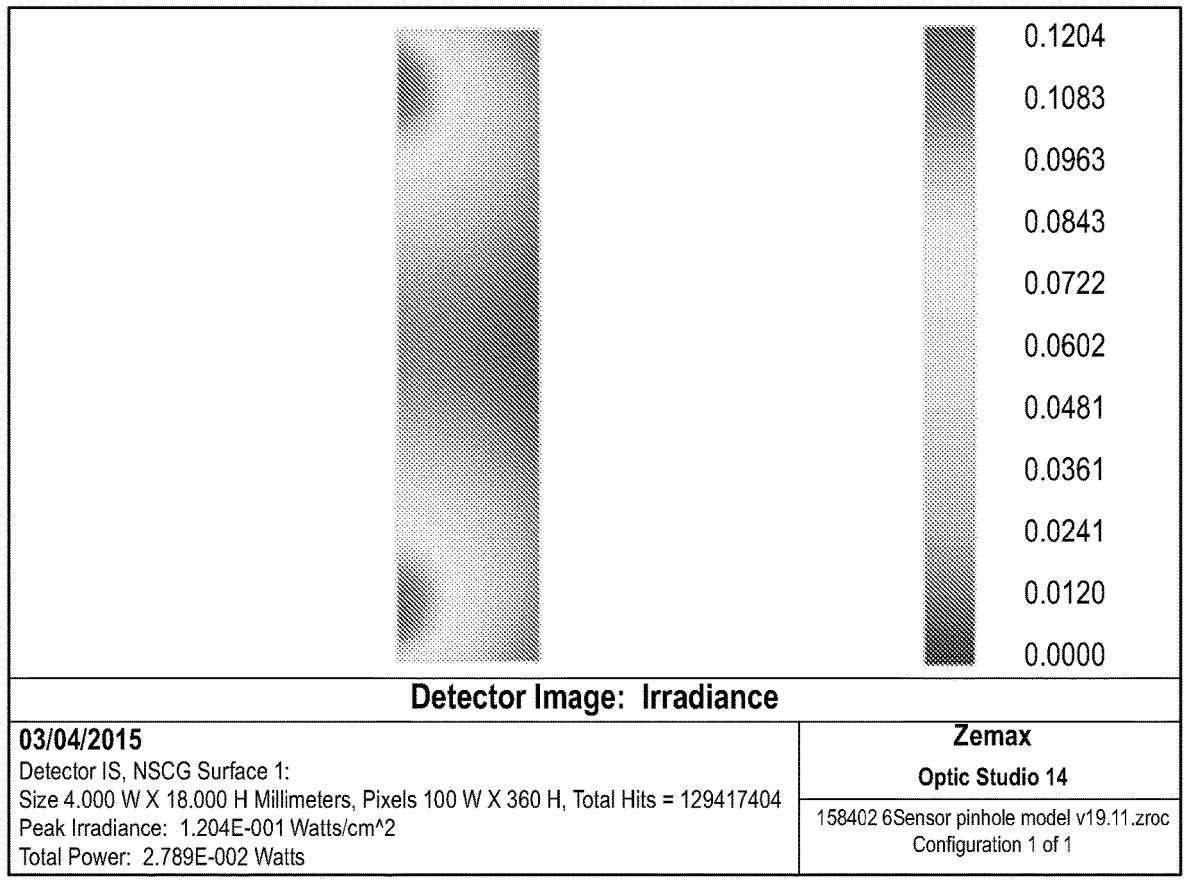
FIG. 22 depicts an example distribution of radiant intensity produced by a variation of a portion of an embodiment of a system for the detection of harmful substances.
Figures 23A, 23B:
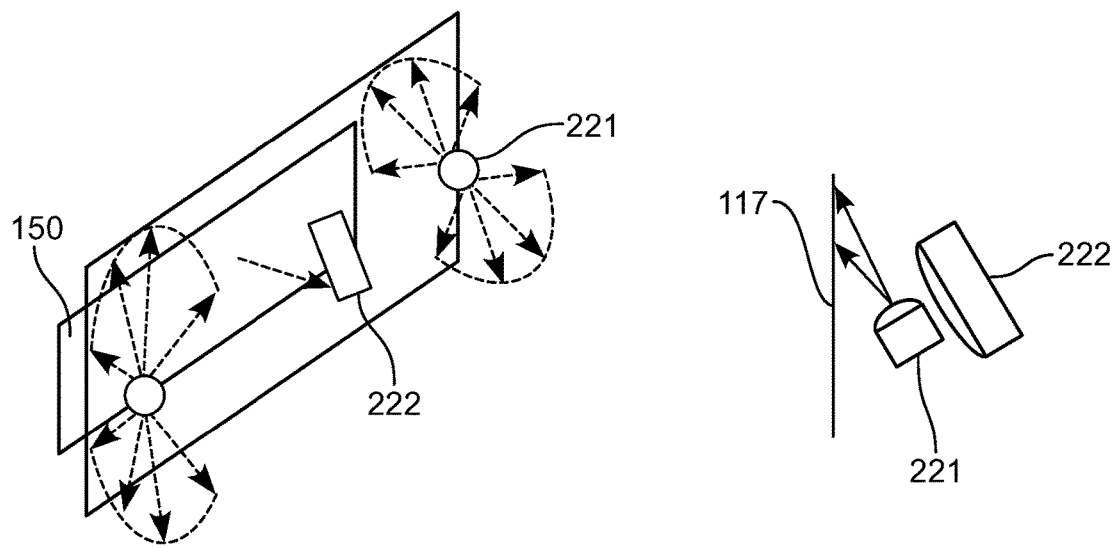
FIGS. 23A and 23B depict a perspective and side view of an example of the optical subsystem.

In a specific example of a distribution of radiant intensity, an illuminator 221 including two LEDs is configured to produce a distribution 2211' such as that shown in FIG. 22, which includes two substantially Gaussian beam profiles. As shown, a first Gaussian beam is incident proximal a first end of the detection substrate and a second Gaussian beam is incident proximal a second end, resulting in a non-uniform radiant intensity distribution at the surface of the detection substrate.

Figure 10A:
FIGS. 10A and 10B depict example outputs of a system for detection of harmful substances.
Figure 10A:
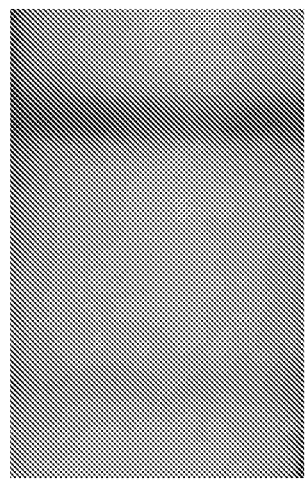
Figure 10B:
Figure 10B:
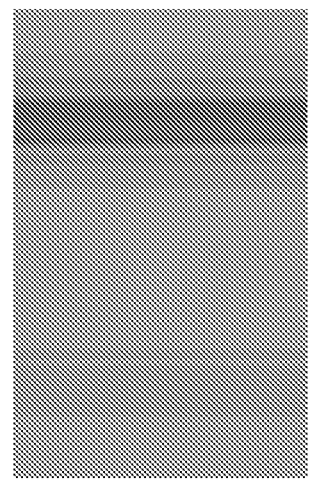

In a first variation, the optical sensing subsystem 220 can include an imager 222 that is configured to image a detection substrate 150 through the detection window 117, and to generate a distribution (e.g., array) of pixel intensities corresponding to regions of the detection substrate. These pixel intensities preferably correspond to the intensities of pixels of a detector 223 of the imager 222. Then, in communication with the processing and control system 240 (described in further detail below), the distribution of pixel intensities generated from processing of a detection substrate 150 can be used to output a value of a parameter associated with an amount (e.g., concentration in parts per million, other concentration, mass, volume, etc.) of a harmful substance present in a consumable sample analyzed using the detection substrate 150. An example of pixel intensity distributions, prior to and post processing at the processing and control system 240, is shown in FIGS. 10A and 10B, respectively.

The imager 222 of the first variation preferably provides data within sufficient resolution to eliminate a requirement for tight coupling between the imager 222 and a detection substrate 150; however, the imager 222 can alternatively provide data with any other suitable resolution. The detector can, in variations, have an active surface (e.g., a surface that actively detects incident light) that is angled (e.g., at an oblique angle) relative to an optical axis between the detection window and the imager, in order to reduce reflections reaching the detector from the detection window. The resolution provided by the imager can be related to the relative arrangement of the imaging aperture of the imager, the detector of the imager, and the detection window, as well as the size of the imaging aperture and the native resolution (e.g., pixel density) of the detector. The spacing between each of the elements along the direction of the optical path between the detection window and the detector mathematically determines the position of the detector relative to the focal plane of the imaging aperture, and can thus result in a substantially focused or a substantially unfocused image on the detector. A substantially focused image at the detector preferably enables the imager to provide an image resolution approaching the native resolution of the detector, whereas a substantially unfocused image can result in "blurring" of image features in the image rendered at the detector. In some variations, a substantially unfocused image is sufficiently resolved to permit detection of image features necessary for substance detection, and can permit a smaller total volume occupied by the imager.

In a specific example, the detector 223 is a CMOS linear image sensor that includes a linear array of pixels (e.g. a 1×N array). In related examples, the detector 223 can be a linear photodiode array, a linear CCD array, or a two-dimensional photodiode/CCD array (e.g., an M×N array). The detector 223 can, however, be any suitable detector of optical signals.

The imager 222 can include an imaging aperture 225 that functions to transform light (e.g., rays of light) into a real image at the detector 223, to enable spatially resolved detection of the received light. The imaging aperture can be created by a mask overlaying the detector, an iris of the detector, a mask overlaying the detection window, a mask positioned between the detector and the detection window, or otherwise formed. The material forming the imaging aperture is preferably impermeable to, diffuses, or absorbs a substantial amount (e.g., 75%, 80%, 90%) of the signal measured by the detector (e.g., be black, when visible light is measured), but can alternatively have any other suitable properties. Examples of material that can be used include felt, paint, paper, plastic, metal, or any other suitable material. As shown in FIG. 4B, the imaging aperture acts as a focusing element for rays of light directed towards the detector from direction of the detection window (e.g., originating from the detection substrate) and focuses the rays into an image at the detector of the imager.

The imaging aperture 225 is preferably a slotted pinhole aperture, but can alternatively be any suitable shape (e.g., a circular pinhole). In the case of a slotted aperture, the longitudinal direction of the slot is preferably substantially orthogonal to the longitudinal axis of the detection window, but can alternatively be oriented in any suitable direction. The imaging aperture 225 is preferably of a size or range of sizes (e.g., 0.5 mm in diameter, 50-500 microns in diameter, etc.) enabling adequate image resolution at the detector while also reducing unwanted reflected light at the detector; however, the imaging aperture 225 can be of any suitable size. The size can be a diameter or average diameter, in the case of a symmetric aperture shape, or can include multiple dimensions (e.g., a slotted pinhole aperture can have a width and a height). For apertures having a height and width, the height (oriented orthogonally to the longitudinal axis of the detection window as previously described) is preferably substantially equal to the lateral dimension (i.e., in a direction orthogonal to the longitudinal axis) of the detection window. However, the height can be less than this dimension, more than this dimension, or any suitable height. There is preferably a single imaging aperture 225 that images a field of view including all active regions of the detection substrate at the detector 223. In other words, the field of view of the detector can be determined by the size and/or position of the aperture (relative to the size and/or position of the detector), which transforms the rays to form the image at the detector as previously described. However, there can alternatively be any number of imaging apertures, each of which can image a field of view including any suitable portion or portions of the detection substrate. For example, the imager can include a different aperture for each distinct region of the detection substrate, wherein the apertures can be aligned with the anticipated locations of the substrate regions along the test container lumen. In variations, the imaging aperture 225 can be augmented with one or more optical elements that modify the image formed at the detector by the aperture (e.g., a lens, f-stop, iris, grating, filter, etc.).

In a specific example, there are three slotted pinhole apertures, each having a field of view corresponding to a single active region of a detection substrate having three active regions. In this example, each slot includes a taper angle, such that the width of the slot reduces in the direction that light travels through the slot from the detection substrate 150 to the detector 223 (e.g., tapers along the thickness of the material defining the slot). However, in related variations, there can be any suitable number of imaging apertures 225 that include any suitable taper (including, for example, no taper).

In the first variation, the imager 222 can be provided along with an illuminator 221 configured to facilitate illumination of the detection substrate 150, in order to enable detection of the analyte(s) at the detection substrate. In specific examples, the illumination module can include one or more light-emitting diodes (LEDs) any/or any other suitable light sources. The LEDs/light sources can be configured to provide white light, or any suitable range of wavelengths of light. Furthermore, in variations wherein the illuminator 221 includes multiple light sources, the light sources can be identical in output (e.g., intensity, wavelength) or non-identical in output. As such, illumination can allow an intensity of a desired signal (e.g., indicative of an analyte associated with a harmful substance) to be enhanced. Illumination can additionally or alternatively function to remove signal interference due to inherent features (e.g., color, acidity, consistency, fermentation, hydrolyzation, etc.) of a consumable sample. For instance, pigmented and/or acidic foods can provide signal interference in a color-based assay. As such, illumination and or detection at a detector 223 of the imager 222 can be enabled in cooperation with one or more filters (e.g., wavelength filters, emission filters, excitation filters, etc.) configured to filter out any interfering signals.

Figure 11A:
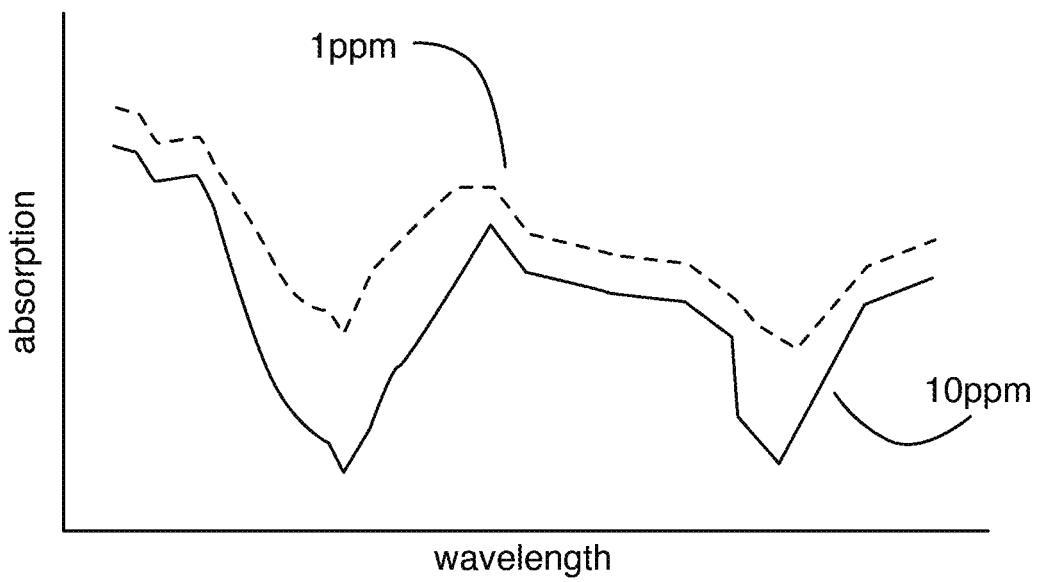
FIGS. 11A-B depict example outputs of a system and/or method for detection of harmful substances.
Figure 11B:
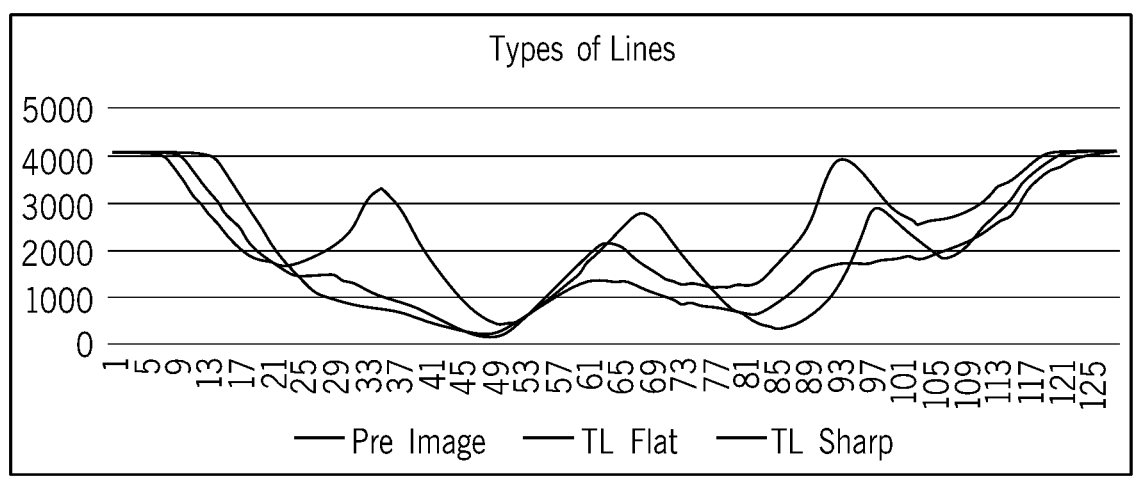

In a second variation, the detector 223 includes a photodiode system 223' configured to detect absorption and/or emission of light (e.g., wavelengths of light) indicative of presence of (i.e., an amount of) an analyte at a detection substrate in communication with the photodiode system 223'. In one variation, the photodiode system 223' can include a photodiode configured to detect absorption of light associated with a peak absorption wavelength of an active region of a detection substrate (e.g., in order to assess absorption at a characteristic peak absorption wavelength of an antibody-coated bead bound to an analyte associated with a harmful substance). In one example for gluten detection, the photodiode system 223' can include a photodiode configured to detect absorption of 555 nm light at a detection substrate, wherein cellulose nanobeads treated with a complementary antibody for gluten have an absorption peak at 555 nm. In this example, a higher degree of absorption of 555 nm light (e.g., as indicated by a lower photodiode output) within an active region of a detection substrate 150 is associated with a higher concentration of gluten in a consumable sample, with an example of output data shown in FIG. 11.

In the second variation, the photodiode system 223' can be provided along with an illuminator 221 configured to facilitate illumination of the detection substrate 150, in order to enable detection of the analyte(s) at the detection substrate. Illumination is preferably provided at an angle (e.g., an acute angle of incidence) relative to a surface of the detection window 117, in order to minimize reflection (e.g., from the detection window 117) that could interfere with sensing by the optical sensing subsystem 220. In specific examples, the illumination module can include one or more light-emitting diodes (LEDs) and/or any other suitable light sources. The LEDs/light sources can be configured to provide light associated with an absorption peak of active particles (e.g., antibody-coated nanobeads, colloidal gold particles) at an active region of a detection substrate 150, or any suitable range of wavelengths of light. These particles can be either chemically conjugated with an antibody or more than one antibody, or can have the antibody or antibodies physically adsorbed onto them. Furthermore, in variations wherein the illuminator 221 includes multiple light sources, the light sources can be identical in output (e.g., intensity, wavelength) or non-identical in output. As such, illumination can allow an intensity of a desired signal (e.g., indicative of an analyte associated with a harmful substance) to be enhanced. Illumination can additionally or alternatively function to remove signal interference due to inherent features (e.g., color, acidity, consistency, fermentation, hydrolyzation, etc.) of a consumable sample. For instance, pigmented and/or acidic foods can provide signal interference in a color-based assay. The signal transduction mechanism can be based on any one or more of: absorption, fluorescence, chemiluminescence, Förster resonance energy transfer, electrical transduction, and any other suitable signal transduction mechanism. As such, illumination and or detection at an optical sensing subsystem 220 of the imager 222 can be enabled in cooperation with one or more filters (e.g., wavelength filters, emission filters, excitation filters, etc.) configured to filter out any interfering signals.

The above variations of the optical sensor can be used in combination and/or provided by the system 100 in any suitable manner. Furthermore, in variations of a detection substrate 150 having multiple active regions, the optical sensor(s) 220 and/or illumination module(s) 222 can be provided in units, wherein the number of units is associated with a number of active regions in a detection substrate. For instance, for a detection substrate 150 having a control region and a test region, the system 100 can include two units, each having a photodiode and a light source (e.g., a 555 nm light source) configured to target each of the two active regions. In variations, however, the optical sensing subsystem 220 can be supplemented with or replaced with any other suitable sensor(s) configured to detect presence of an analyte based upon one or more of: color change, spectral emission, magnetic signals, electrical current, electrical bias, acoustic signals, and any other suitable mechanism.

3.2.D Analysis Device—Processing and Control System

The processing and control system 240 functions to receive signals from the optical sensor 240 and to generate an output indicative of presence of a harmful substance within the consumable sample, based upon signals generated from a detection substrate. The processing and control system 240 can further function to control operation of the analysis device 205, such that detection of one or more analytes associated with harmful substances in a consumable sample is, at least in part, automated. As such, the processing and control system 240 can include a processing module 242 configured to receive signals from the optical sensing subsystem 220 and a control module 244 configured to control operation of the analysis device. The processing and control system 240 is preferably configured to implement at least a portion of the method 300, described in detail in Section 4 below, but can alternatively be configured in any suitable manner.

The processing module 242 is preferably configured to condition signals generated at the optical sensor(s) 220, and can be directly coupled to an output of the optical sensor(s) 220. Alternatively, the processing module 242 can be configured to retrieve data generated from an output of an optical sensing subsystem 220 from a storage module or in any other suitable manner. The processing module 242 can thus be configured to perform any one or more of: denoising, filtering, smoothing, clipping, deconvolving, standardizing, detrending, resampling, and performing any other suitable signal-processing operation on output signals from the optical sensor(s) 220. In variations, wherein an output of the optical sensing subsystem 220 is image data, the processing module 242 can be configured to filter and/or condition image data for sharpness, saturation, edge-finding, intensity, and/or any other suitable image enhancement. The processing module 242 can further be configured to generate an analysis indicative of presence of the harmful substance, wherein the analysis provides information regarding an amount (e.g., concentration, volume, mass) of the harmful substance within the consumable sample. In one variation involving data from a photodiode, the analysis can enable identification of absorption peaks detected upon illumination of a detection substrate 150 (e.g., over time, taking into account kinetics of a reaction at the detection substrate), and associate an amount of absorption with an amount (e.g., concentration in parts per million) of an allergen present in the consumable sample. In one variation involving image data from a camera module, the analysis can characterize intensity (e.g., average intensity, peak intensity, relative intensity) across an active region of a detection substrate, and associate an intensity parameter (or other image parameter) with an amount (e.g., concentration in parts per million) of an allergen present in the consumable sample. The processing module 242 can be implemented in one or more processing elements (e.g., hardware processing element, cloud-based processing element), such that processing by the system 100 can be implemented in multiple locations and/or phases.

In variations, the control module 244 can be configured to control any one or more of: retaining a test container 105 within the analysis device 205 in an alignment configuration, facilitating release of the test container 105 from the analysis device 205 in the releasing configuration, depressing of a plunger 128 of the test container 105 (e.g., to transition a diaphragm 160 of the test container 105 between a first configuration and a second configuration), mixing of the homogenized sample with a process reagent upon transmission of commands to the mixing module 230, activation of a valve 138 of a second chamber 112 of the test container 105 in order to initiate delivery of a volume of a dispersion to a detection substrate 105, illumination of a detection substrate 150 upon transmission of commands to an illumination module 223, transmission of outputs of an optical sensor for conditioning an processing by the processing module 240, and any other suitable operation for automation in use of the system 100.

Modules of the processing and control system 240 can be implemented at any one or more of: on-board at the analysis device 205 that receives a test container 105, at a portion of the test container (e.g., using electronics integrated into the test container 105), and at any other suitable processing subsystem. For instance, modules of the processing and control module 240 can be implemented at a mobile device (e.g., smart phone, tablet, head-mounted computing device, wrist-mounted computing device) in communication with the analysis device 205, such that some amount of data processing and/or control of a test container 105 or analysis device 205 is implemented using the mobile device. Additionally or alternatively, modules of the processing and control system 240 can be implemented in any other hardware-based or cloud-based computing system configured to communicate with the system 100 described.

The processing and control system 240 can additionally or alternatively include a communications module (e.g., a Bluetooth low energy chip) for communication of recorded and/or stored test results to any suitable device (e.g., a user device, a remote server, etc.). However, the processing and control system 240 can be configured in any suitable manner.

Furthermore, the analysis device 205 can include any other suitable elements configured to facilitate processing of a test sample (e.g., a dispersion generated from a consumable sample that has saturated a detection substrate), and/or reporting of information derived from the test sample to a user or other entity. In one variation, the analysis device 205 can include a module configured to facilitate release of the dispersion from the port 136 of the second chamber 112 to a detection substrate 150 at an analysis chamber 115, in cooperation with a valve 138 of the second chamber 112, as described in relation to the port 136 above. The analysis device 205 can further include elements that provide an indication that the analysis device is in an operational mode (e.g., as opposed to an off mode, as opposed to a dormant mode), and/or elements that reduce noise (i.e., signal noise, acoustic noise) during processing of a test sample. The analysis device 205 can further include a housing configured to house elements of the analysis device 205 in a compact manner. The analysis device 205 or any other suitable portion of the system 100 can further include a power module configured to provide power to the system 100 (e.g., by including an energy storing, energy receiving, and/or energy distributing element) such as a battery (e.g., a rechargeable secondary battery, such as a lithium chemistry battery; a primary battery), a piezoelectric device, and/or any other suitable energy storage, generation, or conversion system. As shown in FIG. 14, the analysis device 205 and/or system 100 can additionally or alternatively include a display 250 (e.g., of the analysis device 205, of a mobile device in communication with the system 100) configured to convey information (e.g., results regarding detection of a target substance in the consumable sample) from the system 100 to a user or other entity, and/or any other suitable user interface elements (e.g., input modules, notification modules, buttons 252 for initiating and/or pausing operations of the system 100, etc.) configured to facilitate user interaction with the system 100. In a variation where the analysis device 205 defines a base 206 and two or more triangular faces 207 connected by one or more side walls, a user interface (e.g., an LED display) can be integrated with one or more of the side walls. Additionally or alternatively, the analysis device 205 can include any other suitable elements for processing of a test sample in a manner that is convenient to a user.

As a person skilled in the art will recognize from the previous detailed description and from the figures and claims, modifications and changes can be made to the embodiments of the analysis device 205 without departing from the scope of the analysis device 205.

4. Method

Figure 12:
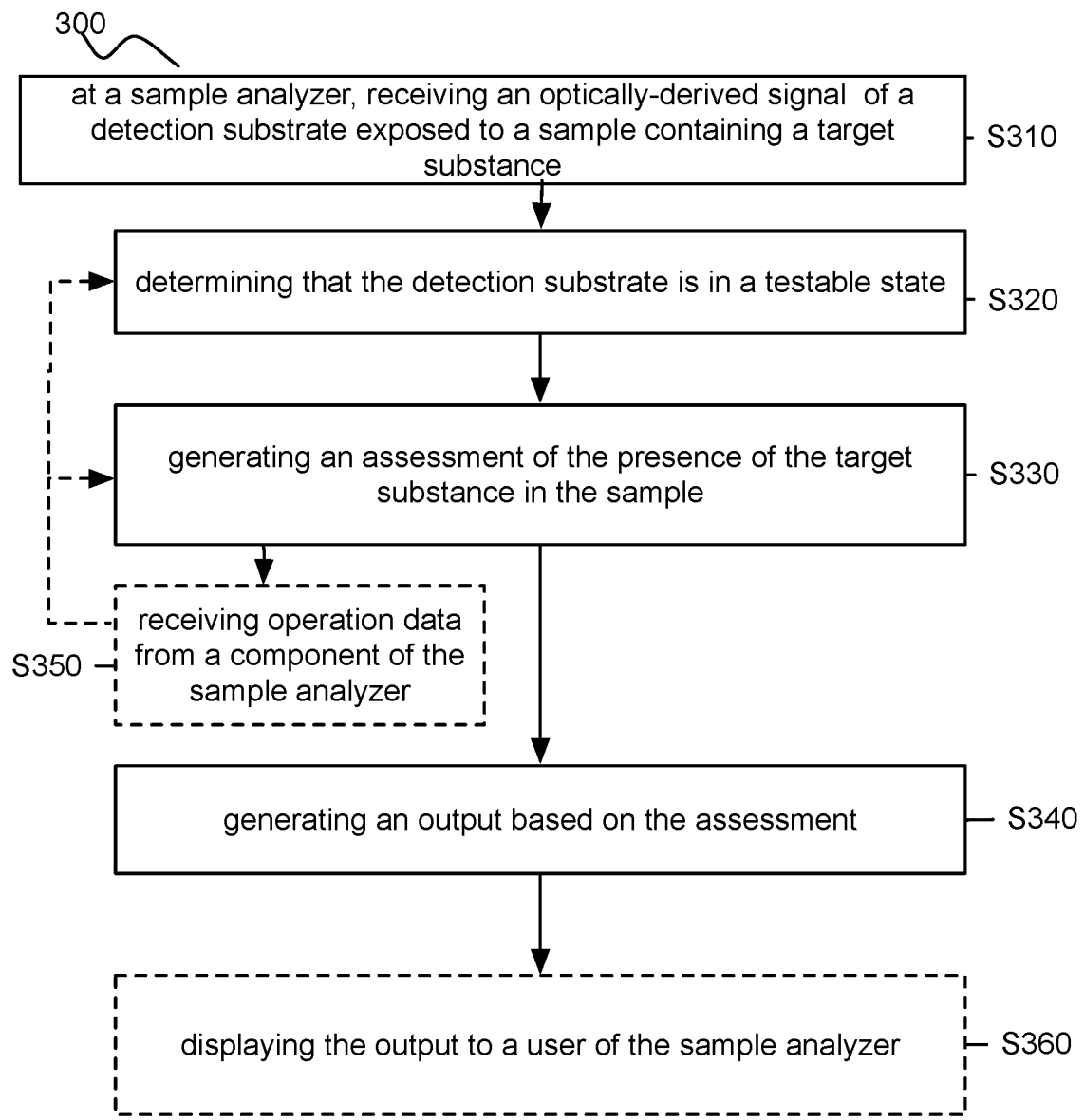
FIG. 12 depicts a flowchart of an embodiment of a method for detection of harmful substances.
Figure 13A:
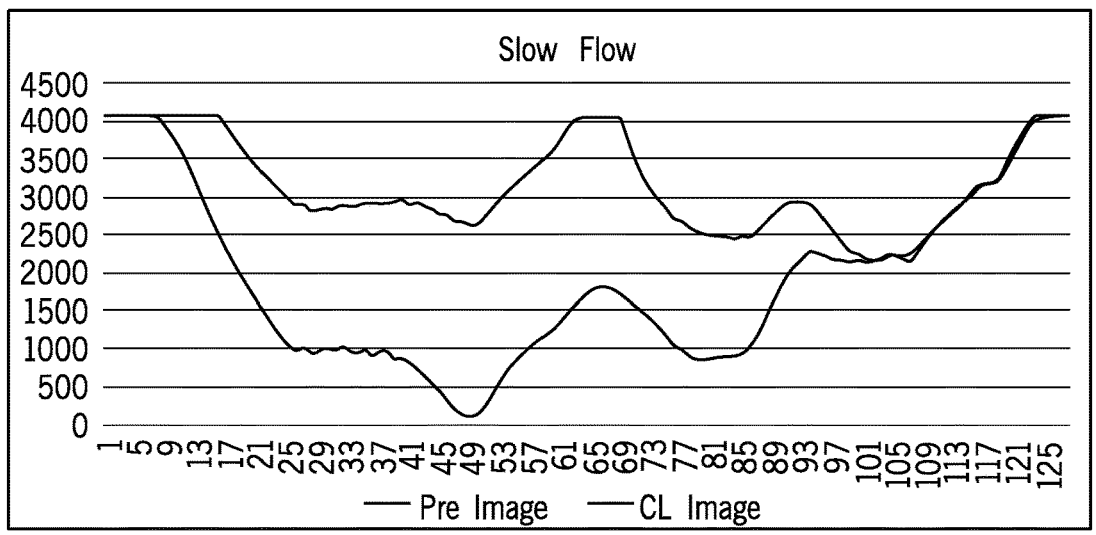
FIG. 13A-C depict example outputs of portions of an embodiment of a method for detection of harmful substances.
Figure 13B:
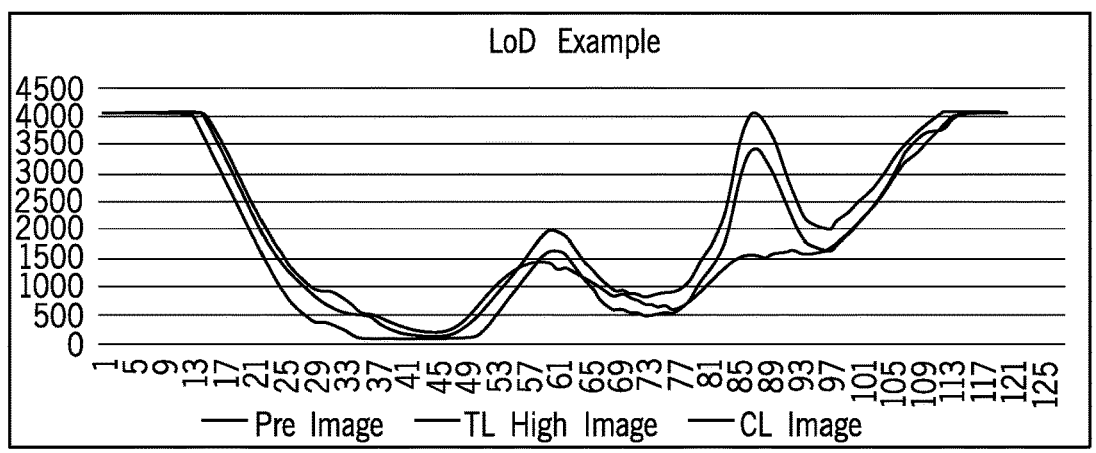
Figure 13C:
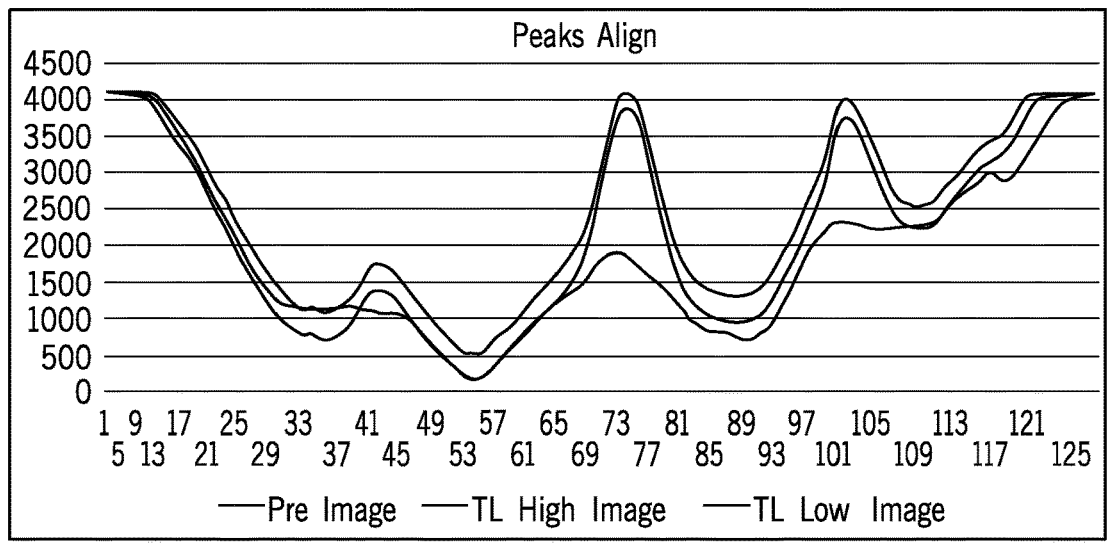

As shown in FIG. 12, an embodiment of a method 300 for detecting a target substance in a consumable sample includes: at a sample analyzer, receiving an optically-derived signal of a detection substrate exposed to a sample containing a target substance S310; determining that the detection substrate is in a testable state S320; generating an assessment of the presence of the target substance in the sample S330; and generating an output based on the assessment S340. The method 300 can optionally include: receiving operation data from a component of the sample analyzer S350; and displaying the output to a user of the sample analyzer S360.

The method 300 functions to enable detection of one or more harmful substances within a processed consumable sample. In examples, the harmful substances can include any one or more of: an allergen (e.g., gluten allergen, a dairy-derived allergen, a nut allergen, a fish allergen, an egg-derived allergen, etc.) a toxin, a bacterium, a fungus, a pesticide, a heavy metal, a chemical or biological compound (e.g., a fat, a protein, a sugar, a salt, etc.), and any other suitable harmful substance. The method 300 is preferably configured to impose minimal requirements upon a consumer using the system 100, in terms of labor-intensiveness, time-intensiveness, and cost-intensiveness. As such, the method 300 is preferably configured to automatically (or semi-automatically) process the image substantially independently from the consumer, and to quickly provide an assessment regarding presence of the harmful substance(s) within the sample. The method 300 is preferably implemented at least in part by the processing module and the optical sensing subsystem of the analysis device 205 of the system 100 described in Section 3 above; however, the method 300 can alternatively be implemented using any other suitable system. In the following sections, a sample analyzer utilized in the method 300 can be an analysis device, such as the analysis device 205 described in Section 3 above, or alternatively any other suitable sample analyzer.

Block S310 recites: at a sample analyzer, receiving an optical signal characterizing a detection substrate exposed to a sample containing a target substance. Block S310 functions to provide data characterizing the detection substrate to a processing module of the sample analyzer, so that the data can be used in subsequent blocks of the method 300. The signal is preferably an image (e.g., a test image) of the detection substrate, but can alternatively be any suitable signal (e.g., a photodiode signal, a set of signals from an array of photodiodes, etc.). As such, Block S310 is preferably implemented at an embodiment, variation, or example of the optical sensing subsystem in cooperation with the processing module described in relation to the system 100 above. In a specific example, the optical signal is preferably received at a detector of the sample analyzer, and preferably is made up of light scattered by the detection substrate after originating from an illuminator of the sample analyzer. In this example, the detector is preferably angled relative to the direction from which the scattered light travels, in order to minimize stray light, unwanted reflections, and the like. In this example, the illuminator preferably generates a non-uniform distribution of radiant intensity at the detection substrate (e.g., an edge-oriented illumination pattern with a greater radiant intensity along a longitudinal edge region of the detection substrate than other portions of the substrate). However, Block S310 can alternatively be implemented with any other suitable system, in any suitable manner.

Note that an image (e.g., a test image, optical signal) of the detection substrate can be any data array that characterizes optical properties of the detection substrate, obtained by way of sensing light that has been emitted, scattered, and/or transmitted by the detection substrate (and/or associated components, such as the detection window). Such optical properties can include: color, reflectivity, absorbance (i.e., how strongly light is attenuated), birefringence, luminosity, photosensitivity, reflectivity, refractive index, scattering, transmittance, and/or any other suitable optical property. These optical properties are preferably represented by and directly related to numerical values of the data array, but can alternatively be represented by any suitable values (e.g., Boolean values). The numerical values can additionally or alternatively be indirectly related to the optical properties of interest; for example, the optical property of interest can be the angle of polarization of light scattered by the detection substrate, and a polarizing filter between an imager of the sample analyzer and the detection substrate can convert the polarization angle of the scattered light into a relative intensity which is measured at the imager (e.g., the intensity of the light that is measured by the imager is proportional to the polarization angle of the light). The image is preferably spatially resolved (e.g., the data array has more than one element in at least two spatial dimensions, and characterizes one or more optical properties in at least two spatial dimensions), but can alternatively represent the optical properties at a single spatial location (e.g., a point, a single pixel, a single array element, etc.). The image can additionally or alternatively characterize non-optical properties (e.g., radiological properties, thermal properties, structural properties, and/or mechanical properties) of the detection substrate, and be captured using any suitable non-optical detector.

Figure 16:
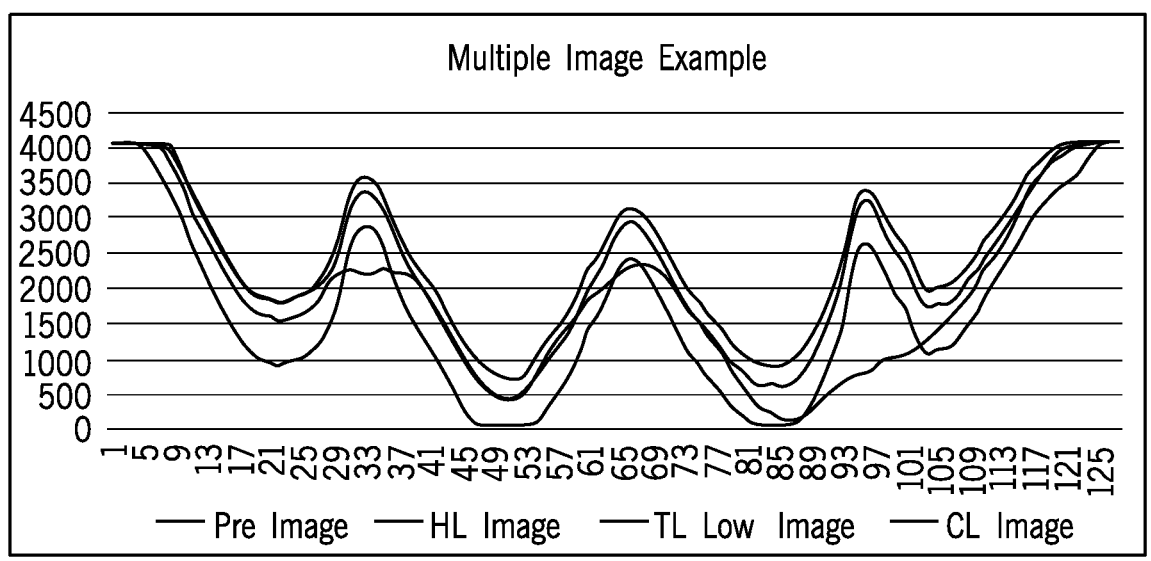
FIG. 16 depicts an example output of a portion of an embodiment of a method for detection of harmful substances.
Figure 17:
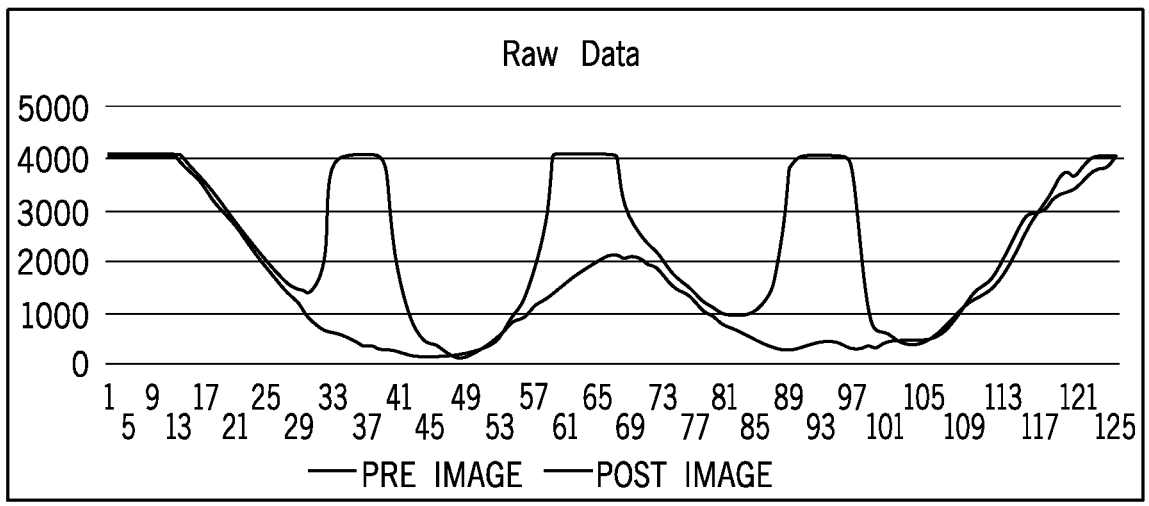
FIG. 17 depicts an example output of a portion of an embodiment of a method for the detection of harmful substances.

Block S310 can additionally or alternatively include: capturing multiple images, as well as capturing images corresponding to distinct regions of the field of view with differing integration times. The integration times of images can be selected dynamically based on the content of the image. For example, the image can contain peaks corresponding to various active regions on the detection substrate, each of which may result in differing absorption strengths. In order to resolve each of the peaks of differing intensity within the image data, a series of images can be captured, each one at an integration time proportional to a background intensity level in the vicinity of the peak, as shown in FIG. 16. In one variation, the method can include recording an image of the detection strip, comparing the image to a reference image, increasing the integration time if the image is below the optimal reference image range, and decreasing the integration time if the image is above the optimal reference image range. This can function to position the reference image such that all bits of the image can be used.

In a specific example, capturing the optical signal (e.g., an image) includes collecting light incident upon a linear photodiode array having a set of pixels, and outputting the test image as a data array to the processing module. In this example, each element of the data array has a one to one correspondence with a pixel in the set of pixels. In this example, the light is collected over a time period (e.g., an integration time), and each element of the data array contains a numerical value that is proportional to the amount of light collected at the linear photodiode array sensor over the time period.

Block S310 is preferably performed substantially immediately after insertion of a test container into the sample analyzer, but can alternatively be performed after a delay (e.g., 10 seconds, 30 seconds, a variable time related to a time period required for mixing, etc.). S310 can be triggered by detecting the test container within the test container lumen (e.g., by a contact switch, optical detector, or any other suitable sensor), by an input provided by a user (e.g., pressing a button that initiates image capture and sample testing), or in any other suitable manner. In variations, S310 can occur periodically, regardless of the presence or absence of a test container in the test container lumen, and the image itself can be used to detect the presence of the test container and initiate subsequent analysis. Additionally or alternatively, S310 can be performed at any suitable time or times.

Block S320 recites: in response to capturing the test image, determining that the detection substrate is in a testable state. Block S320 functions as a preliminary check of characteristics of the detection substrate, in order to determine whether the detection substrate can be reliably and accurately tested for the presence of the target substance. Block S320 is preferably implemented using embodiments, variations, or examples of the processing module 240, the optical sensing subsystem, the detection window, orientation sensor(s), and other components described in relation to the system 100 above; however, Block S320 can alternatively be implemented using any other suitable system. As such, in determining that the detection substrate is in a testable state, Block S320 preferably involves analyzing the captured test image; however, Block S320 can additionally or alternatively determine that the detection substrate is in a testable state in any other suitable manner. The test image captured in S310 is preferably an image of the entire viewable area of the detection substrate, but can additionally or alternatively be of any portion or portions of the detection substrate. For example, a portion of the test image corresponding to a final active region along the flow path of the detection substrate (e.g., the control line) can be used to determine that the dispersion has flowed across the entire substrate, including other active regions (e.g., the test line and/or hook line), and thus that the detection substrate has properly developed and is thus in a testable state. A testable state of the detection substrate is preferably one or more of the following states: properly oriented within a detection window (e.g., the bounds of the active regions are within the viewable area of the detection window), substantially undamaged (e.g., not bent, torn, ripped, broken, warped, etc.; little or no features detected in the image that substantially match and/or are classified as physical strip damage; etc.), and substantially unsaturated (e.g., below a threshold degree of liquid saturation). However, a testable state can be any suitable state of the detection substrate that enables detection of the target substance.

Block S320 can include comparing the test image to a reference image, in order to determine that the detection substrate is in a testable state. The reference image is preferably a prerecorded image stored in system memory, but can alternatively be a previous image of the detection substrate (e.g., recorded more than a threshold time duration prior), an image of a reference strip retained within the analysis system, or any other suitable image. The reference image is preferably an image of the detection substrate in a testable state (e.g., undamaged, fully developed, properly positioned, etc.) and comparison thereto preferably enables the determination of the testability of the detection substrate (e.g., the test image can be determined to be substantially identical and/or similar to the reference image of a detection substrate in a testable state, and therefore the test image can be determined to be of a detection substrate in a testable state). Alternatively, the reference image can be of a detection substrate in an untestable state, and a comparison resulting in a determination that the test image is substantially different from the reference image can lead to the determination that the detection substrate is in a testable state. However, test image and the reference image can alternatively be compared in any suitable manner in order to determine whether the detection substrate is in a testable state.

In variations, Block S320 includes Block S322, which recites: determining a degree of liquid saturation of the detection substrate, recapturing the test image in response to the liquid saturation degree satisfying a recapture condition, and determining that the detection substrate is in a testable state based on the recaptured test image. Block S322 can, in examples, be referred to as performing a "slow flow" check. This can be performed a predetermined period of time after the valve has been opened to trigger strip development (e.g., a predetermined development period, such as 60 seconds). In one variation, S322 can include recording images of the detection substrate at a predetermined frequency and analyzing each image for indicia of a fully-developed strip, alignment with the reference image, and/or any other suitable condition. The degree of liquid saturation is preferably determined based on background intensity values (e.g., intensity values corresponding to regions of the image that do not characterize active regions, as discussed in more detail in relation to Block S330), wherein the recapture condition is satisfied when the liquid saturation degree exceeds a threshold (e.g., indicating excessive reflectivity of the detection substrate related to an over-saturated state of the detection substrate), but can additionally or alternatively be determined in any suitable manner. The degree of liquid saturation can alternatively be determined based on whether a control line has been developed (e.g., has reacted to the sample). The degree of liquid saturation can additionally or alternatively be determined by comparing the test image to a reference image. In such cases, the intensity of the signal of the reference and test images in regions away from the active regions (e.g., intensity of pixels greater than ninety pixels from the edge of the pixel array) can be compared. If a large difference is detected or if a slow flow or low degree of saturation is determined, then the detection substrate is permitted to develop for an additional duration of time (e.g., a delay is implemented). The delay can be calculated based on the magnitude of the difference, the determined degree of liquid saturation, the reflectivity of the detection substrate, the background intensity, or otherwise determined. The delay can be any suitable time delay, such as 10 seconds, 30 seconds, 140 seconds, or any other suitable delay.

In variations of Blocks S310 and S322, the test image is captured at a first time point, and S322 includes determining a delay time based on the determined degree of liquid saturation, and recapturing the test image at a second time point, delayed relative to the first time point by the determined delay time. For example, a degree of liquid saturation can be determined, and found to require a delay time of 15 seconds for the degree of liquid saturation to be reduced below an acceptable level for testing, and the test image can thus be recaptured after a delay of 15 seconds. However, any suitable delay time can be determined and implemented, including a delay time of zero (indicating that the test image does not necessarily need to be recaptured). Preferably, delaying recapturing the test image enables excess liquid to move away from the surface of the detection substrate under capillary action, reducing the degree of liquid saturation. However, delaying image recapture can also enable the degree of liquid saturation to be reduced in any other suitable manner (e.g., evaporation, diffusion, etc.).

In another variation, Block S320 includes Block S324, which recites: determining an orientation of the sample analyzer, and determining that the sample is in a testable state based on the determined orientation of the sample analyzer. The sample analyzer orientation can be determined using the orientation sensor(s) of the sample analyzer (e.g., the accelerometer, gyroscope, IMU, etc.), or otherwise determined. In one embodiment, the sample analyzer can be deemed to be in a testable state when the sample analyzer is upright (e.g., oriented upright; oriented with the retained test container between 0 and 90 degrees of a gravity vector, etc.) and be deemed to be in a nontestable state when the sample analyzer is horizontal or otherwise arranged. Alternatively, the orientation sensor and/or other sensors of the system can be used to trigger sample mixing (e.g., the sample is mixed in response to orientation, insertion, or other preconditions being met). However, the orientation sensor can be used to determine whether the sample analyzer is in any other suitable desired configuration.

In another variation, Block S320 includes Block S326, which recites: determining a structural state of the detection substrate, and determining that the detection substrate is in a testable state based on the structural state of the detection substrate. The structural state preferably characterizes whether the detection substrate has been damaged, altered, or become otherwise constitutionally unable to be analyzed. As such, determining a structural state of the detection substrate can include determining that it has been torn or bent through image recognition techniques (e.g., a distortion of the image due to bending can be recognized as such).

Block S330 recites: generating an assessment of the presence of the target substance in the sample. Block S330 functions to analyze the captured data characterizing the sample and to thereby detect the presence of a target substance in the sample. Block S330 is preferably implemented using embodiments, variations, or examples of the optical sensing system and processing module described in relation to the system 100 above; however, Block S330 can alternatively be performed using any other suitable system 100. As such, Block S330 can include receiving homogenized portions of a consumable sample within a cavity of a diaphragm configured between the first chamber and the second chamber, and delivering homogenized portions of the consumable sample into the second chamber by depressing a plunger configured to contact the diaphragm. Block S330 can, however, include delivering the homogenized sample from the first chamber to a second chamber of the test container in any other suitable manner.

In generating an assessment in Block S330, the assessment preferably provides information regarding an amount (e.g., concentration, volume, mass) of the harmful substance within the consumable sample. In one variation involving data from a photodiode, generating the assessment in Block S330 can include identifying absorption peaks detected upon illumination of a detection substrate 150 (e.g., over time, taking into account kinetics of a reaction at the detection substrate and/or development time of exposed substrate), and associating an amount of absorption with an amount (e.g., concentration in parts per million) of an allergen present in the consumable sample. In one variation involving image data from a camera module, generating the assessment in Block S330 can include characterizing intensity (e.g., average intensity, peak intensity, relative intensity) across an active region of a detection substrate, and associating an intensity parameter (or other image parameter) with an amount (e.g., concentration in parts per million) of an allergen present in the consumable sample. Association between an amount of absorption and/or intensity is preferably performed by comparison to a reference amount (e.g., a reference image, a lookup table), but can alternatively be performed by comparison to an input value (e.g., by a user, received from a remote portion of the processing module). In alternatives, the processing module of the sample analyzer can receive and store user (and/or automated) feedback as to the accuracy of the association, and perform future associations between an amount of absorption and/or intensity and an amount of allergen by way of machine learning (e.g., a training algorithm, neural network, etc.). In related variations, the machine learning algorithm that associates signal values with allergen concentrations can be implemented on a network of processing modules, which can include the processing module of the sample analyzer, in order to incorporate data from a network of users, sample analyzers, and/or any other suitable data sources. Block S330 can, however, include processing signals derived from a detection substrate saturated with a volume of the dispersion, and/or generating an assessment in any other suitable manner.

In variations, Block S330 can include processing the image data to enhance morphological features of the data. These morphological features are preferably peaks (e.g., maxima) in the data, but can additionally or alternatively be any suitable morphological features. Processing preferably includes one or more of: background correction, filtering (e.g., kernel convolution), and dynamic-integration-time multi-image capture; however the image data can be processed in any suitable manner. These processing techniques are described in further detail below.

Block S330 can include processing the image data using background correction. Background correction is preferably the subtraction of a reference image (e.g., an image of an undeveloped detection substrate) from a test image (e.g., an image of a developed test substrate), in order to enhance the relative magnitude of any signal present in the data above the background signal level as well as to account for any fixed-pattern noise in the image (e.g., smudges on the detection window, scratches on transparent objects in the optical path, etc.).

In variations, Block S330 can include determining (e.g., identifying, locating) portions of the image data (e.g., sets of adjacent pixels, portions of the data array, etc.) that correspond to signals collected from active regions of the detection substrate S331. Block S331 can function to reduce the quantity of image data that is analyzed in other blocks of the method 300 by distinguishing the portions image data corresponding to the active regions from the portions corresponding to inactive regions (e.g., regions of the detection substrate that do not express a particular optical characteristic when exposed to a sample containing a target substance, background regions, noise regions, etc.). This can enable efficient detection of the target substance in this and other blocks of the method 300. The active regions of the detection substrate are preferably active regions as described above in relation to the detection substrate 150 of the system 100, but can alternatively be any suitable regions of the detection substrate configured to express an optical quality of interest when the detection substrate is exposed to the sample. The detection substrate can include any number of active regions (e.g., one, three, five, fifty, etc.), and S330 can include determining portions of the image data corresponding to any number of the active regions (e.g., all the active regions, a subset of the active regions).

In a variation, the detection substrate can include a number of active regions, and identifying portions of the image data corresponding to the number of active regions includes identifying a first portion of the image corresponding to the first active region, and identifying the remaining portions based on a predetermined, known spacing (e.g., in units of image pixels) between the first active region and the remaining active regions. The first active region preferably exhibits a strong (e.g., high intensity, large absorbance) signal that enables its efficient detection by signal processing (e.g., peak finding) techniques described in relation to this and other blocks, as well as determination of its location within the image (e.g., in image coordinates). For example, the first active region can correspond to the control line of the detection substrate, which can be configured to generate an unambiguous signal (e.g., a strong peak of one or more orders of magnitude greater intensity than a typical test signal) to facilitate ease of detection and/or location. However, the first active region can be identified in any other suitable manner. In a specific example of identifying other portions of the image based on the location of the first portion corresponding to the active region, the first portion of the image (corresponding to a first active region) can be separated from a second portion of the image (corresponding to a second active region, such as a test region) by 20 pixels, and from a third portion of the image (corresponding to a third active region, such as a hook region) by 50 pixels; thus, the portions of the image corresponding to each of the active regions can be determined based on the known spacing. Additionally or alternatively, other techniques can be employed to determine one or more portions of the image data corresponding to active regions of the detection substrate, such as peak-edge detection, thresholding, or any other suitable image and/or signal processing techniques.

Figure 15:
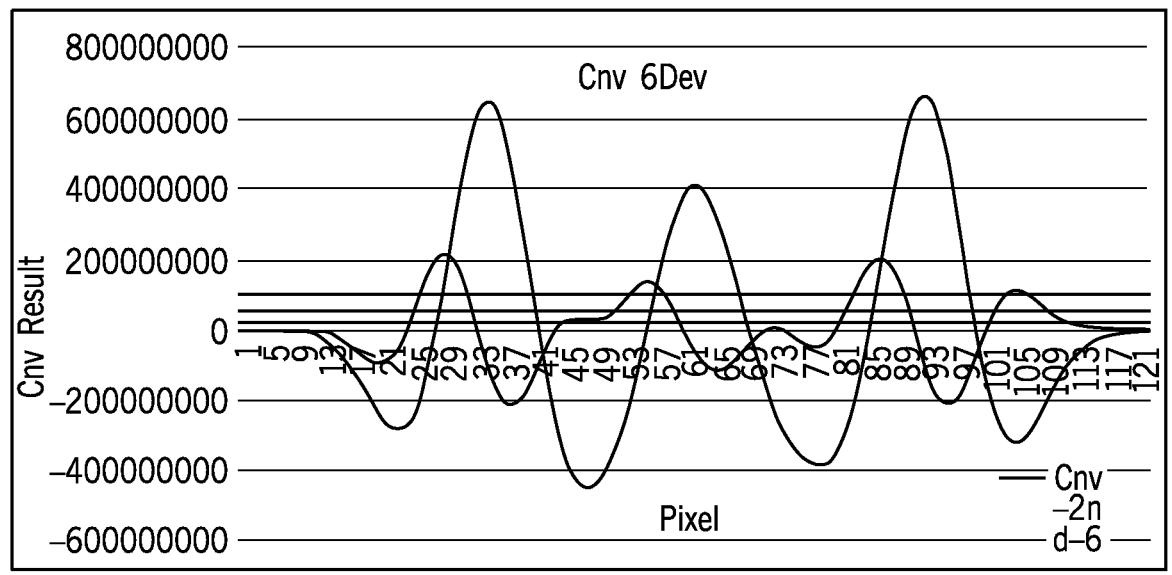
FIG. 15 depicts an example output of a portion of an embodiment of a method for detection of harmful substances.

In generating the assessment, peak detection can be performed on the optical signal and/or image data in order to identify absorption peaks and the relative locations thereof within the image data. Peak detection is preferably performed by way of kernel convolution, but can alternatively be performed using any suitable peak-finding technique. In a first variation, peaks are identified using kernel convolution as depicted in FIG. 15 in which a kernel (e.g., a Gaussian kernel, a derivative of a Gaussian kernel, a top hat kernel) of a specified functional shape is convolved with the image data (e.g., by the processing module of the sample analyzer) in order to accentuate, and thereby detect, image features (e.g., morphological features) of substantially the same shape as the kernel. One or more kernels can be used, in order to detect peaks of various shapes. In some cases, the shape of the absorbance peak can be related to the source of the target substance. For example, certain consumables can be characterized by narrow peaks present in the image data upon detection of a target substance, while other consumables can be characterized by broad peaks. The kernel can thus be selected according to a known consumable undergoing analysis; additionally or alternatively, multiple kernels of different shapes (e.g., widths, functional forms) can be used, and the results of each convolution used to determine the identity of the consumable undergoing testing.

S330 can include peak detection, as described above, and can thus include Block S332, which recites: identifying a first location of a peak signal value in an upstream test image, identifying a second location of a peak signal value in a downstream image, and comparing the first and second locations to generate a peak confidence metric. Block S332 functions to determine if a peak signal value detected in the test image is an accurate positive result, based on whether the location of the detected peak signal value is substantially the same between multiple images. The peak signal value is preferably within a portion of the image data corresponding to an active region, having preferably been located in S331, the portion having an upstream edge (e.g., a pixel of the image corresponding to the upstream-most edge of the active region of the detection substrate) and a downstream edge (e.g., a pixel of the image corresponding to the downstream-most edge of the active region of the detection substrate). However, the peak signal value can alternatively be within any other suitable portion of the image, corresponding to any suitable region of the detection substrate. The peak confidence metric can be a confidence factor (e.g., a number between 0 and 1, 0% and 100%, etc.) or a binary metric (e.g., True, False), or any other suitable metric. The upstream test image can be captured with a first integration time, and the downstream test image can be captured with a second integration time. In the context of digital imaging, integration time as used herein is, in general, the time duration over which light is collected at the optical sensor before being output as a signal. Preferably, the first integration time is related to a background signal level on an upstream edge of the image portion containing the peak, and the second integration time is related to a background signal level on a downstream edge of the image portion containing the peak. The utilization of distinct integration times can enable a peak residing in a portion of the image with a non-uniform background signal to be efficiently identified. Alternatively, however, the integration times can be substantially identical. Alternatively, the integration times can be dynamically adjusted (and corresponding images sampled) until the signal from the image region substantially matches that of the corresponding reference image region. Preferably, any peak detection performed in generating the assessment is associated with a peak confidence metric, in that a detected peak is preferably associated with a high (e.g., greater than a threshold value, such as 50%, 0.25, etc.) peak confidence metric. In some cases, an otherwise probable peak (e.g., based on the result of kernel convolution) can be discarded if the peak confidence metric associated with the peak is low (e.g., lower than a threshold value, such as 90%, 0.75, etc.). Alternatively, the assessment can be generated based at least in part on the peak confidence metric in any suitable manner, or independently of (e.g., not based on) the peak confidence metric. In some implementations, the image can be realigned relative to a reference image (e.g., the intensity values associated with an original set of pixel locations shifted to a different set of pixel locations) as a result of the peak confidence metric, and the peak confidence metric can be determined again in relation to the realigned image.

In variations and/or alternatives, Block S330 can include any one or more of: denoising, filtering, smoothing, clipping, convolving, deconvolving, standardizing, detrending, averaging, resampling, and performing any other suitable signal-processing operation on output signals from an optical sensor in communication with a detection substrate saturated with the dispersion. In variations of Block S330 involving image data, Block S330 can include filtering and/or conditioning image data for sharpness, saturation, edge-finding, intensity, and/or any other suitable image enhancement.

Block S340 recites: generating an output based on the assessment. Block S340 functions to create a result of the assessment, and to provide the result for use in other blocks of the method 300 (e.g., displaying the output S350). Block S340 is preferably implemented using embodiments, variations, or examples of the second chamber 112, the mixing element 1101, and/or the mixing module 230 described in relation to the system 100 described above, however, Block S340 can alternatively be implemented using any other suitable system. The generated output can be a binary output (e.g., a positive test result, a negative test result), a ternary output (e.g., a positive test result, a negative test result, an indeterminate test result), a quantitative output (e.g., a number of ppm of the target substance detected), a combination of the aforementioned outputs (e.g., a positive test result also indicating a concentration of the target substance), or any other suitable output. The output is preferably provided to the user of the sample analyzer, but can additionally or alternatively be stored, transmitted, or analyzed in any suitable manner as part of S340.

Block S350 recites: receiving operation data from the sample analyzer. Block S350 functions to provide feedback data (and/or feedforward data) to other blocks of the method 300 based on operation of various components of the sample analyzer. Block S350 is preferably implemented using embodiments, variations, or examples of the mixing module 230 and/or the optical sensing subsystem 240 described in relation to the system 100 above; however, Block S350 can alternatively be implemented using any other suitable system. As such, Block S350 can include receiving operational data from sensors, the mixing module, valves, switches, or any other components related to the operation of the system 100. Other blocks of the method 300 can, in turn, be performed based on the received operation data of S350. For example, operation data can include data indicating that the test container has been improperly coupled (e.g., inserted) into the sample analyzer (e.g., received by way of a switch residing in a test container lumen of the sample analyzer configured to detect the presence and proper insertion of a test container), and determining that the detection substrate is in a testable state S320 can be based on this operation data.

In a variation, Block S350 can include receiving mixing data from a mixing module of the sample analyzer. In particular, In particular, S350 can include detecting proper coupling between the complementary magnet of a mixing module and a magnetic mixing element within a test container; this can be performed by way of sensing of a magnetic force, by way of detection of motion of the magnetic mixing element in response to motion of the complementary magnet, or in any other suitable manner. Mixing data is preferably data characterizing whether mixing of the homogenized sample was successfully performed; however, mixing data can be any other suitable data. Successful mixing performance can be related to the duration for which mixing was performed by the mixing module; in such cases, mixing data can include data indicating that the mixing module was operating nominally for a duration of time consistent with successful mixing. Mixing data can additionally or alternatively characterize operating parameters of the mixing module (e.g., a time series signal of the power and/or current drawn by a motor of the mixing module), which can in turn characterize successful mixing. Preferably, the assessment generated in S330 is based on the mixing data, in that a negative test (e.g., a test indicating that no target substance was detected) is invalidated in the event that the mixing data indicates that mixing was unsuccessful. Alternatively, the integration times can be adjusted (e.g., increased, decreased, etc.) based on the mixing data. However, the generated assessment can additionally or alternatively be based on the mixing data in any suitable way, or the assessment can be generated independently of (i.e., not based on) the mixing data. Received mixing data can additionally or alternatively be used to provide feedback to the system, and/or trigger the execution of additional and/or existing blocks. In an example, mixing data indicating that the mixing was performed inadequately is received, and the mixing module is then controlled (e.g., by the sample analyzer and/or a processing module thereof) to remix the sample (e.g., perform mixing for an additional time duration). In a related example, data indicating that a motor of the mixing module has stalled (e.g., electrical current data showing excessive current draw) is received, and in response the motor is pulsated (e.g., rhythmically, sporadically, etc.) to ensure adequate mixing. The received mixing data can additionally or alternatively be incorporated as feedback to this and other blocks in any suitable manner.

Operation data can include orientation data, pertaining to the physical orientation of the sample analyzer during performance of the method 300. Such orientation data can be incorporated as an input to various blocks, as a form of feedback or otherwise. In variations, orientation data can include the relative orientation of the sample analyzer relative to a gravity vector, and can be used to determine whether the sample analyzer was positioned substantially upright during mixing and/or detection substrate development. The assessment generated in S330 can be based on the aforementioned determination; for example, if the sample analyzer is not upright and is a variant of sample analyzer that utilizes gravitational force to urge the sample dispersion into contact with the detection substrate, the generated assessment may indicate that the detection substrate was not properly exposed. The orientation data can additionally or alternatively be dynamically incorporated into generating the assessment; for example, orientation data can be received indicating that the sample analyzer was placed on its side (e.g., accidentally knocked over) during testing, and assessment generation can thus be restarted in response, upon proper reorientation of the sample analyzer.

In a related variation, received orientation data can trigger the execution of additional and/or existing blocks of the method 300. For example, orientation indicating that the sample analyzer is on its side (e.g., not oriented at least partially along a gravity vector) can cause a notification to be provided to a user that the sample analyzer should be reoriented before testing can continue. Such a notification can be incorporated into generating the assessment as described above. The orientation data can additionally or alternatively be incorporated into and/or trigger any suitable blocks, in any suitable manner.

Block S360 recites: providing the output to a user of the sample analyzer. Block S360 functions to provide the result of the analysis to a user, in order to enable the user (e.g., consumer of the source of the consumable sample being analyzed) to perform actions based on the result (e.g., safely consume or not consume the source of the sample). Block S360 is preferably implemented using embodiments, variations, or examples of the processing and control system described in relation to the system 100 above; however, Block S360 can alternatively be performed using any other suitable system.

4.1 Method—Specific Implementations

In a first specific implementation of the method 300, insertion data is received indicating that a test container has been inserted into the sample analyzer, and in response a first image (e.g., pre-image) of an (undeveloped) test strip is captured by the optical sensing subsystem of the sample analyzer. After receiving mixing data from the mixing module of the sample analyzer, indicating that the sample has been mixed and exposed to the detection substrate, a second image (e.g., post image) is captured. The second image is compared to the first image by subtracting the pre image from the post image to produce a background corrected image. If the subtraction results in a substantially zero value of intensity in the background corrected image in a region of the image corresponding to a test line (e.g., one of the active regions) of the strip, an assessment is generated that the presence of the target substance has not been detected. If the subtraction results in a value of intensity in the above image region that exceeds a threshold value (e.g., a peak is detected), an assessment is generated that the presence of the target substance has been detected.

Figure 18:
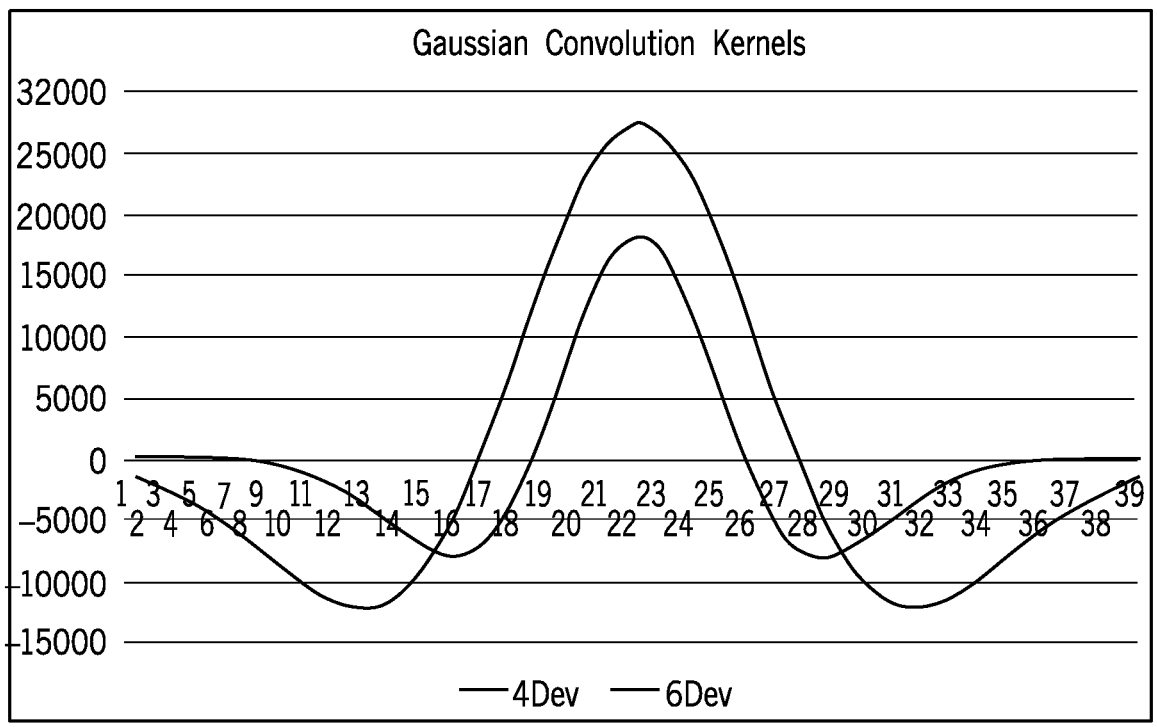
FIG. 18 depicts an example output and/or input of a portion of an embodiment of a method for detection of harmful substances.

In a second specific implementation, a background corrected image (obtained in a manner such as described in relation to the first specific implementation) is filtered using a convolution filter. In filtering the data, it is convolved with the second derivative of a Gaussian kernel of a width of six standard deviations, corresponding to a wide (e.g., 20 pixels) peak. In a related implementation, the data is convolved with a similar kernel having a width of 4 standard deviations, corresponding to a narrow peak (e.g., 10 pixels). In a further related implementation, the data is convolved with both kernels as described. Examples of the shape and relative size of the described kernels are shown in FIG. 18.

While blocks of the method 300 can occur as distinct steps, in some variations, portions of at least Blocks S310, S320, S330, S340, S350, and/or S360 can be performed substantially simultaneously. The blocks of the method 300 can additionally or alternatively be performed in any suitable order. Any block can be performed based on the output of any other block, alone or in combination.

The method 300 can additionally or alternatively include any other suitable blocks or steps configured to facilitate detection of the presence of one or more harmful substances within the consumable sample.

Embodiments of the system 100 and/or method 300 and variations thereof can be embodied and/or implemented at least in part by a machine configured to receive a computer-readable medium storing computer-readable instructions. The instructions are preferably executed by computer-executable components preferably integrated with the system 100 and one or more portions of the processing module 242. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which includes one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Although omitted for conciseness, the preferred embodiments include every combination and permutation of the various system components and the various method processes, wherein the method processes can be performed in any suitable order, sequentially or concurrently.

As a person skilled in the art will recognize from the previous detailed description and from the figures and claims, modifications and changes can be made to the preferred embodiments of the invention without departing from the scope of this invention defined in the following claims.

We claim:
1. A system comprising:
   a test container including:
      a chamber having a reagent therein, the chamber configured to receive a sample; and
      a detection substrate including a test strip, the detection substrate fluidly coupled to the chamber of the test container, the detection substrate configured to detect an analyte;
   a housing including a lumen that is configured to removably receive the test container;
   an image sensor coupled to the housing and configured to be optically coupled to the detection substrate when the test container is positioned within the housing, wherein when the test container is removed from the lumen of the housing, the detection substrate is optically decoupled from the image sensor; and
   a processor in communication with the image sensor, the processor being configured to:
      receive, from the image sensor, an image of the detection substrate;
      generate, using the image, an assessment of a presence of the analyte within the sample; and generate an output indicative of a positive test result or a negative test result of the presence of the analyte within the sample, based on the assessment.

2. The system of claim 1, wherein the detection substrate includes an active region having an antibody that is complementary with the analyte; and
wherein generating the assessment of the presence of the analyte within the sample includes:
identifying a portion of the image that corresponds to the active region of the detection substrate; and
identifying a peak within the portion of the image that corresponds to the active region.

3. The system of claim 2, wherein the detection substrate includes a control region; and
wherein the portion of the image is a first portion and the peak is a first peak;
wherein generating the assessment of the presence of the analyte within the sample includes:
identifying a second portion of the image that corresponds to the control region of the detection substrate; and
identifying a second peak within the second portion of the image that corresponds to the control region.

4. The system of claim 1, wherein the processor is further configured to display the output to a user of the system.

5. The system of claim 1, further comprising an illuminator coupled to the housing and optically coupled to the detection substrate, the illuminator being configured to illuminate the detection substrate.

6. The system of claim 1, wherein the output is indicative of the positive test result of the presence of the analyte within the sample;
wherein generating the assessment of the presence of the analyte within the sample includes determining at least one of an amount of the analyte within the sample or a concentration of the analyte within the sample.

7. The system of claim 1, wherein generating an assessment of the presence of the analyte within the sample includes:
analyzing the image;
detecting the presence of the analyte within the sample, based on the analyzing of the image; and
generate the output indicative of the positive test result, based on the detecting the presence of the analyte within the sample.

8. The system of claim 1, wherein the image is a test image; and
wherein the processor is further configured to:
compare the test image to a reference image of the detection substrate or another detection substrate;
analyze the test image to determine a degree of liquid saturation of the detection substrate; and
determine that the detection substrate is in a testable state, based on the comparison between the test image and the reference image and the degree of liquid saturation of the detection substrate; and
wherein generating the assessment of the presence of the analyte within the sample is based on the determination that the detection substrate is in a testable state.

9. The system of claim 1, wherein generating the assessment of the presence of the analyte within the sample includes filtering the image.

10. The system of claim 1, wherein the analyte is at least one of a food allergen or is gluten.

11. A system comprising:
a test container including:
a body;
a chamber having a reagent therein, the chamber configured to receive a sample;
a detection substrate including a test strip, the detection substrate fluidly coupled to the chamber of the test container, the detection substrate configured to detect an analyte; and
an analysis device including:
an image sensor optically coupled to the detection substrate;
a housing including a lumen that is configured to removably receive the test container, wherein when the test container is removed from the lumen of the housing, the detection substrate is optically decoupled from the image sensor; and
a processor in communication with the image sensor, the processor being configured to:
receive, from the image sensor, an image of the detection substrate;
analyze the image of the detection substrate; and
determine a presence of the analyte within the sample, based on the analyzing of the image of the detection substrate.

12. The system of claim 11, wherein the detection substrate includes an active region having an antibody that is complementary with the analyte.

13. The system of claim 11, further comprising an illuminator optically coupled to the detection substrate, the illuminator being configured to illuminate the detection substrate.

14. The system of claim 11, wherein the processor is further configured to:
generate an output including a positive test result corresponding to the presence of the analyte within the sample; and
provide the output to a user.

15. The system of claim 14, wherein the processor is further configured to:
determine, using the image of the detection substrate, at least one of an amount or a concentration of the analyte within the sample; and
wherein the output includes at least one of the amount or the concentration of the analyte within the sample.

16. The system of claim 11,
wherein the image sensor is coupled to the housing and configured to be optically coupled to the detection substrate when the test container is positioned within the housing.

17. The system of claim 11, wherein the analyte is at least one of a food allergen or is gluten.

18. A system comprising:
a test container including:
a body;
a chamber having a reagent therein, the chamber configured to receive a sample;
a detection substrate including a test strip, the detection substrate fluidly coupled to the chamber of the test container, the detection substrate configured to detect an analyte;
an analysis device including:
an optical sensor optically coupled to the detection substrate;
a housing including a lumen that is configured to removably receive the test container; and a processor in communication with the optical sensor, the processor being configured to:
receive, from the optical sensor, an optical signal characterizing the detection substrate exposed to the sample;
analyze the optical signal; and
detect a presence of the analyte within the sample, based on the analyzing of the optical signal.

19. The system of claim 18, wherein the detection substrate includes an active region that includes an antibody that is complementary with the analyte;
wherein the optical sensor is configured to detect an absorption of light associated with a peak absorption wavelength of the active region; and
wherein the system includes a light source configured to illuminate the detection substrate with light associated with the peak absorption wavelength of the active region.

20. The system of claim 18, wherein the analyte is at least one of a food allergen or is gluten;
wherein the optical sensor is an image sensor; and
wherein the optical signal is an image.

\* \* \* \* \*